(12) United States Patent
Brodie et al.

(10) Patent No.: US 8,110,550 B2
(45) Date of Patent: Feb. 7, 2012

(54) HDAC INHIBITORS AND HORMONE TARGETED DRUGS FOR THE TREATMENT OF CANCER

(75) Inventors: Angela Brodie, Fulton, MD (US); Vincent Njar, Glen Burnie, MD (US); Gauri Sabnis, Catonsville, MD (US); Lalji Gediya, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 516 days.

(21) Appl. No.: 12/134,717

(22) Filed: Jun. 6, 2008

(65) Prior Publication Data

US 2009/0048156 A1 Feb. 19, 2009

Related U.S. Application Data

(60) Provisional application No. 60/942,452, filed on Jun. 6, 2007, provisional application No. 61/013,570, filed on Dec. 13, 2007.

(51) Int. Cl.
*A61P 35/00* (2006.01)
*A61K 38/00* (2006.01)
*A61K 39/00* (2006.01)
*G01N 33/574* (2006.01)
*C07K 16/28* (2006.01)

(52) U.S. Cl. .............. 514/19.4; 424/174.1; 424/138.1; 435/7.23; 530/389.7

(58) Field of Classification Search .................. None
See application file for complete search history.

(56) References Cited

U.S. PATENT DOCUMENTS

| | | | |
|---|---|---|---|
| 6,905,669 | B2 | 6/2005 | DiMartino |
| 2002/0183388 | A1 | 12/2002 | Gudas et al. |
| 2005/0038113 | A1 | 2/2005 | Groner et al. .............. 514/546 |
| 2006/0199829 | A1 | 9/2006 | Anandan et al. |
| 2007/0092498 | A1 | 4/2007 | Giordano |
| 2007/0123580 | A1 | 5/2007 | Atadja et al. |
| 2007/0135431 | A1 | 6/2007 | Smith et al. |
| 2007/0190022 | A1 | 8/2007 | Bacopoulos et al. |
| 2008/0085874 | A1 | 4/2008 | Kushner et al. ............ 514/177 |
| 2010/0184812 | A1 | 7/2010 | Njar et al. .................. 514/357 |

FOREIGN PATENT DOCUMENTS

| | | |
|---|---|---|
| EP | 1485370 | 12/2004 |
| WO | WO 03/076400 | 9/2003 |
| WO | WO-2003/076430 | 9/2003 |
| WO | WO 2004/103358 | * 12/2004 |
| WO | WO-2004103358 | 12/2004 |
| WO | WO-2005023179 | 3/2005 |
| WO | WO 2006/082428 | 8/2006 |
| WO | WO-2006127977 | 11/2006 |
| WO | WO 2007/056135 | 5/2007 |
| WO | WO-2007056243 | 5/2007 |
| WO | WO-2007115286 | 10/2007 |
| WO | WO-2007120557 | 10/2007 |
| WO | WO 2008/027837 | 3/2008 |
| WO | WO-2008154402 | 12/2008 |

OTHER PUBLICATIONS

Goss, 2000, Breast cancer research and treatment, 64, 177-188.*
Richie, 2003, Clinical cancer research, 9, 6105s-6106s.*
Retrived from: http://www.mdanderson.org/patient-and-cancer-information/cancer-information/cancer-types/pancreatic-cancer/index.html, 6 pages, retrived on Jan. 5, 2011.*
Geisler, 1998, Clinical Cancer research, 4, 2089-2093.*
Imyanitov, 2004, Drug Discovery Today, 1, 235-245.*
International Preliminary Report on Patentability, issued Dec. 17, 2009 (published Dec. 17, 2009) during the prosecution of International Application No. PCT/US2008/066156.
Bankhead, "SABCS: Agent Aims at Restoring Hormone-Sensitive Status of Breast Cancer Tumor Cells," Published by Medpage Today. Dec. 15, 2007. Article can be found at: http://www.medpagetoday.com/MeetingCoverage/SABCS/7710.
Banwell et al, "Antiproliferative Signalling by 1,25(OH)2D3 in Prostate and Breast Cancer is Suppressed by a Mechanism Involving Histone Deacetylation," Recent Results Cancer Res. 2003;164:83-98.
Chen et al., "Chemical Ablation of Androgen Receptor in Prostate Cancer Cells by the Histone Deacetylase Inhibitor LAQ824," Mol Cancer Ther. Sep. 2005;4(9):1311-9.
Fabian, "Breast Cancer Chemoprevention: Beyond Tamoxifen," Breast Cancer Res. 2001;3(2):99-103. Epub Jan. 17, 2001.
Handratta et al, "Novel C-17-Heteroaryl Steroidal CYP17 Inhibitors/Antiandrogens: Synthesis, In Vitro Biological Activity, Pharmacokinetics, and Antitumor Activity in the LAPC4 Human Prostate Cancer Xenograft Model," Abstract. J Med Chem. Apr. 21, 2005; vol. 48(8):2972-84.
Hodges- Gallagher et al, "Inhibition of Histone Deacetylase Enhances the Anti-Proliferative Action of Antiestrogens on Breast Cancer Cells and Blocks Tamoxifen-Induced Proliferation of Uterine Cells," Breast Cancer Res Treat. Nov. 2007;105(3):297-309. Epub Dec. 21, 2006.
International Search Report issued Dec. 10, 2008, during the prosecution of International Application No. PCT/US2008/066156. Published Feb. 26, 2009.
International Search Report issued Oct. 27, 2008, during the prosecution of International Application No. PCT/US2008/066120. Published Dec. 18, 2008.
Lee et al., "MS-275, A Histone Deacetylase Inhibitor, Selectively Induces Transforming Growth Factor Beta Type II Receptor Expression in Human Breast Cancer Cells," Cancer Res. Feb. 1, 2001;61(3):931-4.

(Continued)

Primary Examiner — Cecilia J Tsang
Assistant Examiner — Satyanarayana Gudibande
(74) Attorney, Agent, or Firm — Fulbright & Jaworski L.L.P.

(57) ABSTRACT

The present invention relates to the methods of treating endocrine-regulated cancers, including hormone resistant cancers, for example. More specifically, the present invention relates to a method of increasing the sensitivity of hormone resistant cancers to hormonal therapeutic agents. In particular embodiments, the present invention concerns delivery of a histone deacetylase inhibitor and a hormone targeted drug to an individual with cancer. In specific embodiments, the histone deacetylase inhibitor and the hormone targeted drug act synergistically to treat the cancer, including by overcoming resistance to a cancer therapy.

16 Claims, 20 Drawing Sheets

OTHER PUBLICATIONS

List et al., "Inhibition of Histone Deacetylation Augments Dihydrotestosterone Induction of Androgen Receptor Levels: An Explanation for Trichostatin A Effects on Androgen-Induced Chromatin Remodeling and Transcription of the Mouse Mammary Tumor Virus Promoter," Exp Cell Res. Nov. 1, 1999;252(2):471-8.

Marrocco et al., "Suberoylanilide Hydroxamic Acid (Vorinostat) Represses Androgen Receptor Expression and Acts Synergistically With an Androgen Receptor Antagonist to Inhibit Prostate Cancer Cell Proliferation," Mol Cancer Ther. Jan. 2007; vol. 6(1):51-60.

Nakayama et al., "Epigenetic Regulation of Androgen Receptor Gene Expression in Human Prostate Cancers," Lab Invest. Dec. 2000;80(12):1789-96.

Nelson-Degrave et al., "Valproate Potentiates Androgen Biosynthesis in Human Ovarian Theca Cells," Endocrinology. Feb. 2004;145(2):799-808. Epub Oct. 23, 2003.

Patel et al., "New 4-Azolyl Retinoids (Retinoic Acid Metabolism Blocking Agents): Emerging Candidates for Breast Cancer Chemoprevention and Therapy," Proc Amer Assoc Cancer Res, vol. 45, 2004.

Rashid et al, "Synergistic Growth Inhibition of Prostate Cancer Cells by 1 Alpha,25 Dihydroxyvitamin D(3) and Its 19-Nor-Hexafluoride Analogs in Combination With Either Sodium Butyrate or Trichostatin A," Oncogene. Apr. 5, 2001;20(15):1860-72.

Rokhlin et al., "Mechanisms of Cell Death Induced by Histone Deacetylase Inhibitors in Androgen Receptor-Positive Prostate Cancer Cells," Mol Cancer Res. Feb. 2006;4(2):113-23.

Written Opinion issued Dec. 10, 2008, during the prosecution of International Application No. PCT/US2008/066156.

Written Opinion issued Oct. 27, 2008, during the prosecution of International Application No. PCT/US2008/066120.

Zhang et al., "Enhanced Therapeutic Effect on Androgen-Independent Prostate Cancer by Depsipeptide (FK228), A Histone Deacetylase Inhibitor, in Combination With Docetaxel," Urology. Aug. 2007;70(2):396-401.

"Drug slows prostate tumor growth by keeping vitamin A active," *Findings from the AACR Centennial Conference on Translational Cancer Medicine: From Technology to Treatment*, Singapore, Press Release, Nov. 2007.

Belosay et al., "Effects of novel retinoic acid metabolism blocking agent (VN/14-1) on letrozole-insensitive breast cancer cells," *Cancer Research*, 66(23):11485-11493, 2006.

Belosay et al., "Histone deacetylation inhibitors synergize with retinoic acid metabolism blocking agent (VN/14-1) in letrozole resistant human breast cancer cells," Poster, *The Endocrine Society's 88th Annual Meeting*, Boston, MA, US, Jun. 2006.

Belosay et al., "Histone deacetylation inhibitors synergize with retinoic acid metabolism blocking agent (VN/14-1) in letrozole resistant human breast cancer cells," Abstract, *The Endocrine Society's 88th Annual Meeting*, Boston, MA, US, May 2006.

Brodie, "Preclinical modeling of endocrine response and resistance," presentation, 2007.

Chang et al., "Gene expression signature of fibroblast serum response predicts human cancer progression: similarities between tumors and wounds," *PLoS Biology*, 2(2):206-214, 2004.

Coffey et al., "Histone deacetylase inhibitors and retinoic acids inhibit growth of human neuroblastoma in vitro," *Med. Pediatr. Oncol.*, 35(6):577-581, 2000.

Coffey et al., "The histone deacetylase inhibitor, CBHA, inhibits growth of human neuroblastoma xenografts in vivo, alone and synergistically with all-trans retinoic acid," *Cancer Res.*, 61:3591-3594, 2001.

Goss et al., "Liarozole fumarate (R85246): in the treatment of ER negative, tamoxifen refractory or chemotherapy resistant postmenopausal metastatic breast cancer," *Breast Cancer Res Treat*, 64(2):177-188, 2000.

Kitamura et al., "Histone deacetylase inhibitor but not arsenic trioxide differentiates acute promyelocytic leukaemia cells with t(11;17) in combination with all-*trans* retinoic acid," *Br. J. Haematol.*, 108:696-702, 2000.

Knies-Bamforth, "Fight against cancer taking centre stage in Boston," *Drug Discovery Today*, 9(23):998-999, 2004.

Leary et al., "Mechanisms of endocrine resistance," *Advances in Breast Cancer*, 4(2):31-39, 2007.

Macedo et al., "Downregulation of the androgen receptor activity in Ac1 cells results in resistance to DHT and letrozole," *American Association for Cancer Research Annual Meeting*, Abstract #3660, Apr. 2006.

Nagy et al., "Nuclear receptor repression mediated by a complex containing SMRT, mSin3A, and histone deacetylase," *Cell*, 89:373-380, 1997.

Njar, "Novel atypical RAMBAs endowed with potent anti-cancer activities," *FASEB Summer Research Conferences*, Abstract, 2006.

Ritchie et al., "The histone deacetylase inhibitor PXD101 synergises with established chemotherapeutics to inhibit tumor cell proliferation and upregulate apoptosis in vitro," *Clinical Cancer Research, The American Association for Cancer Research*, Abstract #A150; 9(16), 2003.

Sabnis et al., "Combination of HDACi entinostat (SNDX-275) with letrozole provides superior control over tumor growth in ER negative MDA-MB-231 xenograft model," *San Antonio Breast Cancer Symposium*, Poster, Dec. 2008.

Sabnis et al., "Expression of ER and aromatase in MDA-MB-231 tumors by HDACI entinostat leads to growth inhibition by aromatase inhibitor letrozole," Johns Hopkins University Retreat, Abstract and Presentation, Jun. 2009.

Sabnis et al., "Expression of ERα and aromatase in MDA-MB-231 tumors by HDAC inhibitor entinostat leads to growth inhibition by aromatase inhibitor letrozole," *San Antonio Breast Cancer Symposium*, Poster, Dec. 2009.

Sabnis et al., "HDAC inhibitors sensitive ER negative breast cancer cells to AIs," *San Antonio Breast Cancer Symposium*, Poster, Dec. 14, 2007.

Sabnis et al., "HDAC inhibitors sensitive ER negative breast cancer cells to AIs," *San Antonio Breast Cancer Symposium*, Abstract, 2007.

Sabnis et al., "Strategies to delay acquired resistance to letrozole through intermittent treatment in breast cancer xenografts," *American Association for Cancer Research Annual Meeting*, Poster and two pages from presentation, Apr. 2008.

Sabnis et al., "Upregulation of ERα and aromatase by HDACi MS-275 in an ER negative breast cancer xenograft model," *The Endocrine Society's 90th Annual Meeting*, San Francisco, Poster, Jun. 2008.

Sabnis et al., "Upregulation of ERα and aromatase by HDACi MS-275 in an ER negative breast cancer xenograft model," *The Endocrine Society's 90th Annual Meeting*, San Francisco, Abstract, 2008.

Supplementary European Search Report issued in European Application No. EP 08 77 0366, mailed Jul. 23, 2010.

Sabnis et al., "Functional activation of ER-alpha and aromatase by the HDAC inhibitor entinostat increases the sensitivity of ER-negative tumors to letrozole," *Cancer Res.*, Published Online First Jan. 18, 2011. doi:10.1158/0008-5472.CAN-10-2458, 22 pages.

Brodie, Angela M. H.; "Aromatase Inhibitors and Their Application to the Treatment of Breast Cancer"; 2002; pp. 251-269; Copyright 2002; Marcel Dekker, Inc. (XP009149911); New York, NY.

Budillon, Alfredo et. al.; "Histone Deacetylase Inhibitors: A New Wave of Molecular Targeted Anticancer Agents"; 2007; pp. 119-134; vol. 2; Bentham Science Publishers Ltd.

Sharma, Dipali et. al.; "Restoration of Tamoxifen Sensitivity in Estrogen Receptor-Negative Breast Cancer Cells: Tamoxifen-Bound Reactivated ER Recruits Distinctive Corepressor Complexes"; Jun. 15, 2006; pp. 6370-6378, vol. 66(12); Cancer Res. 2006 (XP-002629900).

* cited by examiner

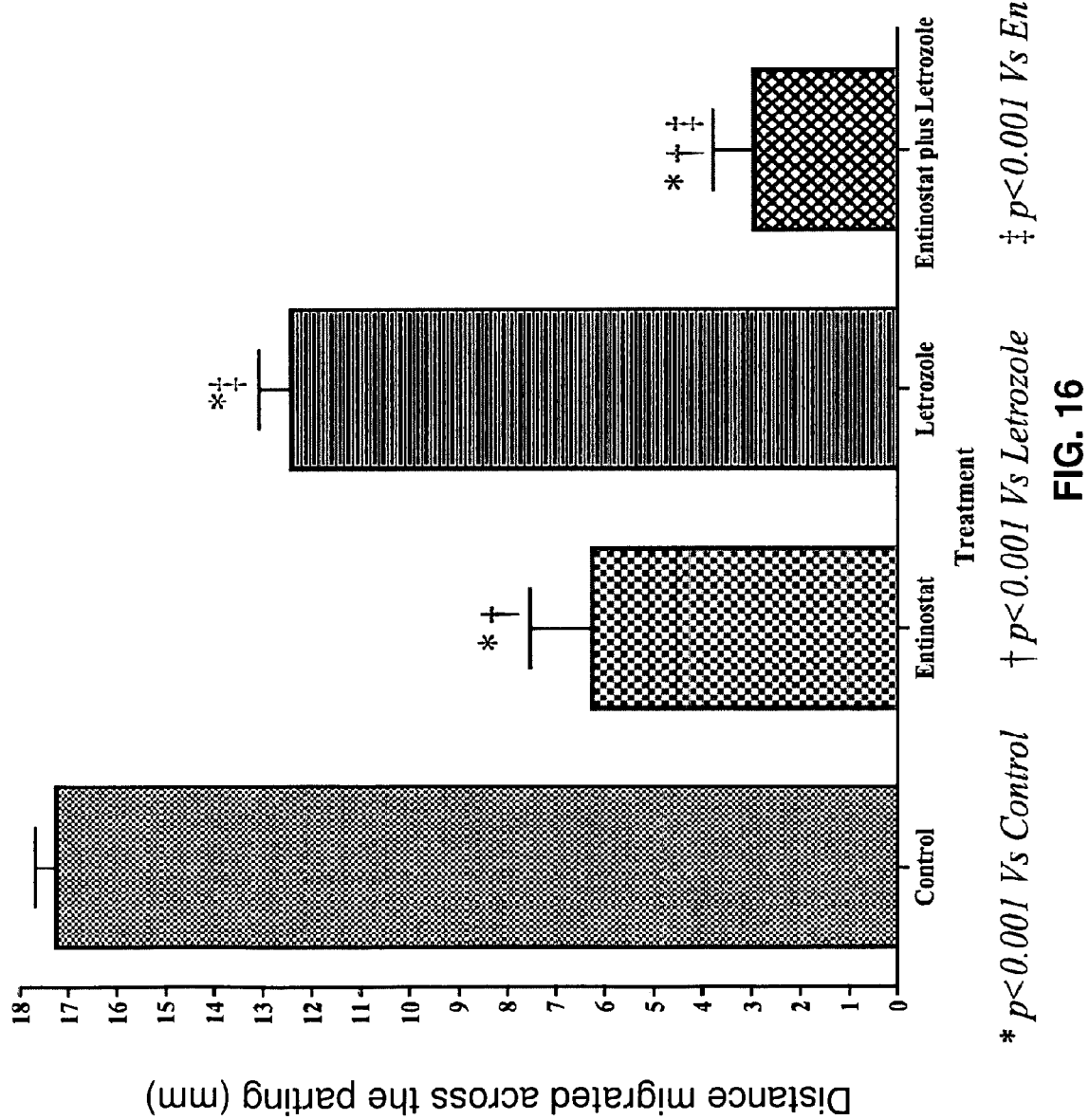

HDAC INHIBITORS AND HORMONE TARGETED DRUGS FOR THE TREATMENT OF CANCER

This application claims priority to U.S. Provisional Patent Application Ser. No. 60/942,452, filed Jun. 6, 2007, and to U.S. Provisional Patent Application Ser. No. 61/013,570, filed Dec. 13, 2007, both of which applications are incorporated by reference herein in their entirety.

STATEMENT REGARDING FEDERALLY SPONSORED RESEARCH OR DEVELOPMENT

This invention was made in part with government support under Grant Nos. R01 CA-62483 and R21 CA117991 awarded by the National Institutes of Health. The United States Government has certain rights in the invention.

TECHNICAL FIELD

The present invention relates at least to the fields of medicine and oncology. More specifically, the present invention relates to methods and compositions of treating cancers, including hormone-resistant cancers, for example. In addition to treating the exemplary hormone-resistant cancers, the present invention can be used to increase the sensitivity of cancers to therapy, such as increasing the sensitivity of hormone-resistant cancers to hormonal therapeutic agents, by administering a combination of one or more histone deacetylase inhibitors and one or more hormonal therapeutic agents.

BACKGROUND OF THE INVENTION

Hormone resistance is a particular problem in cancers such as prostate cancer and breast cancer.

Androgens, acting via androgen receptors, are essential for normal growth and function of the prostate gland and have been implicated in the progression of prostate cancer. Selective androgen receptor modulators (SARMs)—drugs intended to inhibit the activity of androgen receptors—are therefore standard treatment for prostate cancer. However, prostate cancers often become resistant to such treatment. A similar phenomenon can also occur in breast cancers treated with drugs that target the hormone receptor for estrogen.

A. Breast Cancer

Breast cancer is the most prevalent form of cancer among women in the United States and second leading cause of cancer related deaths (Jemal et al., 2006). According to 2006 cancer statistics, approximately 40,000 women are expected to die from breast cancer in the US (Jemal et al., 2006). In the year 2003, although a marked 7% decrease in the incidence of breast cancer was reported, this decrease mainly was associated with estrogen receptor positive (ER+) breast cancers (Ravdin et al., 2006). Estrogen receptor-negative (ER−) breast cancer still is essentially incurable and aggressive. Although, breast cancer treatment has undergone significant improvement, resistance develops to almost all forms of cancer therapy. Additionally, there has been little improvement in the treatment of ER− breast cancer. The high prevalence of breast cancer and development of resistance to effective treatments provides a strong stimulus for the development of additional, targeted therapies with minimal toxicity.

Hormone resistance is a particular problem in cancers such as breast cancer. The antiestrogen tamoxifen, intended to inhibit the activity of estrogen receptor, is standard treatment for breast cancer. However, breast cancers often become resistant to such treatment.

The knowledge that estrogens contribute a pivotal role in development of breast cancer has been exploited clinically by the development of endocrine agents, predominantly by estrogen withdrawal or antagonism (Jordan et al., 2007). Antiestrogen tamoxifen has been used to treat breast cancer for a number of years now. More recently, AIs such as letrozole and anastrozole have surpassed the beneficial effects of tamoxifen and are now being used in the clinic as the first line treatment for hormone dependent post-menopausal breast cancer (Goss et al., 2005; Goss et al., 2002). AEs/AIs are currently used for postmenopausal ER positive breast cancer agents (Brodie, 1990; Baum, 2002; Baum et al., 2002). The clinical use of these agents is limited by development of resistance and the presence of ER− cancer phenotype. Loss of AE/AI sensitivity has been associated with lack of ER expression.

B. Prostate Cancer

Prostate cancer is the most commonly diagnosed cancer in North American men and it is estimated that there are over 300,000 newly diagnosed cases each year (Landis, et al., 1998; Shibata, et al., 1998). The incidence and mortality rates from prostate cancer are increasing and this is due, in part, to an increasingly aging population and the higher incidence of this disease in older men (Gao et al., 1997; Chiarodo, 1991). Both benign prostatic hypertrophy (BPH) and prostate cancer are decreased or not detected in eunuchs and are linked not only to advancing age but the presence of testes and androgen function (Gao et al., 1997; Chiarodo, 1991; Sakti and Crawford, 1993).

Early prostate cancer tends to be androgen-dependent and requires expression of a functional androgen receptor (AR), whereas later stage tumors progress to androgen-independence which in some cases is correlated with loss of AR function (Cheng et al., 1993). Interestingly, the progression from early stage hormone-dependent to latter stage hormone-independence in prostate cancer in men is also observed for breast cancer in women where estrogen-responsiveness undergoes a similar pattern of change in women with early or late stage disease (Hopp and Fuqua, 1999; Fuqua et al., 1995).

Prostate cancer therapy is dependent on the stage of the tumor and AR expression. Early stage androgen-responsive prostate cancers can be treated by castration or with antiandrogens or drugs that block androgen-induced responses including steroidal antiandrogens (cyproterone), LHRH analogs, nonsteroidal antiandrogens (flutamide, nilutamide, bicalutamide), and the potent estrogenic drug diethylstilbestrol (reviewed in (Sadar et al., 1999; Klotz, 2000; Morris et al., 2000; Boccardo, 2000). In addition, there are several possible novel strategies for treatment of prostate cancer and other tumor-types and these include targeting of critical genes involved in tumor cell growth and metastasis (e.g., antiangiogenic drugs, antisense therapy) (Boasberg et al., 1997; Knox et al., 1998; 1998; Yamaoka et al., 1993; Folkman, 1995; Folkman, 1971). Ligands for nuclear receptors (NR) are also being developed for treatment of prostate cancer through inhibitory NR-AR crosstalk that involves various ligands or drugs that bind the retinoid acid/X-receptors (retinoids), vitamin D receptor (calcitrol), and peroxisome proliferator activate receptor γ (trogilatazone) (Dorai et al., 1997; Pienta et al., 1993; Pollard et al., 1991; Kelly et al., 1996; Miller et al., 1992; Miller et al., 1995; Peehl et al., 1994; Gross et al., 1998; Kubota et al., 1998; Tontonoz et al., 1997; Tontonoz et al., 1994; Smith et al., 1999).

The present invention is the first to use a combination of hormonal therapy and histone deacetylase inhibitors to treat hormone resistant cancers.

SUMMARY OF THE INVENTION

In particular cases, the present invention concerns treating endocrine-regulated cancers, including, by way of non-limiting example, breast, prostate, ovarian and endometrial cancers. In specific embodiments, the endocrine-regulated cancer is resistant to one or more therapies, whereas in other embodiments the cancer is sensitive to one or more therapies. In further specific embodiments, the endocrine-regulated cancer is resistant to one or more endocrine therapies, whereas in other embodiments the cancer is sensitive to one or more endocrine therapies. In particular embodiments, the cancer is hormone-resistant cancer, such as estrogen-resistant cancer or progesterone-resistant cancer, for example.

In certain aspects of the invention, there are methods and compositions that overcome resistance to a cancer therapy, including an endocrine therapy, using histone deacetylase inhibitors (HDACi) in combination with a hormone-targeted drug. In additional aspects, the present invention concerns enhancing response of a cancer to therapeutic agents, and in specific aspects the present invention concerns enhancing response of a cancer to endocrine agents. In further aspects, the present invention concerns synergism between HDACi and hormone-targeted drugs for the treatment of cancer, and in particular for the treatment of a cancer that is endocrine regulated, including one that is resistant to the corresponding endocrine hormone.

The present invention relates to the use of HDACi to alter the sensitivity of estrogen receptor negative cells or androgen receptor negative cells to hormonal therapies. For example, the HDACi increase ER and aromatase expression and/or activity, thus making the tumors or neoplasms more sensitive to aromatase inhibitors in addition to antiestrogens. In some embodiments, the combination of HDACi and hormonal therapies have an additive or synergistic inhibitory effect on hormone dependent cells and tumors.

One embodiment of the present invention comprises a method of treating a hormone resistant cancer comprising the step of administering to a subject having or suspected of having the hormone resistant cancer a histone deacetylase inhibitor and a hormone targeted drug in an effective amount to treat the cancer. The hormone resistant cancer is breast cancer, in a specific embodiment. More specifically, the breast cancer is estrogen receptor negative. Still further, the breast cancer can be refractory.

In certain preferred embodiments, the hormone therapy comprises an aromatase inhibitor or an anti-androgen.

In certain embodiments, the hormone targeted drug is an aromatase inhibitor. Aromatase inhibitors include compounds that inhibit the action of the enzyme aromatase, which converts androgens into estrogens by aromatization. Aromatase inhibition by a particular compound can be determined by using methods known in the art including measuring the release of tritium-labeled water upon the conversion of tritium-labeled androstenedione to estrone in the manner provided for in U.S. Pat. No. 6,803,206, which is incorporated herein by reference in its entirety.

Exemplary aromatase inhibitors useful in the invention can include, but are not limited to, anastrozole (Arimidex), letrozole (Femara), exemestane (Aromasin), formestane (Lentaron), and testolactone (Teslac). Other compounds that have shown promise as aromatase inhibitors that may be used in the present invention include, but are not limited to atamestane, vorozole (Rivizor), fadrozole (16949A), roglethimide, pyridoglutethimide, trilostane, aminoglutethimide (Cytadren), 4-Hydroxyandrostenedione (4-OHA; Formastane), finrozole, and YM-511 (4-[N-(4-bromobenzyl)-N-(4-cyanophenyl)amino]-4H-1,2,4-triazole).

In certain embodiments, the hormone targeted drug is an anti-androgen. As used herein, the term "anti-androgen" refers to a compound that that can prevent or inhibit the biologic effects of androgens inhibiting activity of the C17, 20-lyase or 5-reductase enzymes. In specific embodiments, the term comprises a compound that inhibits binding between androgen and an androgen receptor. As used herein, a 17-alpha-hydroxylase-C17,20-lyase inhibitor is a compound that directly or indirectly inhibits the activity of either one or both of the enzymes C17,20-lyase or 5-reductase, which converts testosterone (T) to 5-alpha-dihydrotestosterone. Examples of hydroxylase/lyase and/or 5-reductase inhibitors can be found in U.S. Pat. No. 5,994,334; U.S. Pat. No. 5,264,427; and WO 2006/093993. Compounds that inhibit the androgen receptor can be identified using methods known in the art including one or more in vitro cell-assays that profile ligand mediated modulation of the androgen receptor, including, but not limited to (i) N—C interaction, (ii) transcriptional repression, and (iii) transcriptional activation, as set forth in U.S. Publ. No. 2008/0125399, which is incorporated herein by reference. Inhibition of C17,20-lyase activity can be determined by methods known in the art including measuring the release of tritium-labeled acetic acid during the conversion of tritium-labeled hydroxypregnenolone to dehydroepiandrosterone using liquid scintillation spectrometry in the manner provided for by Nnane et al which is incorporated herein by reference in its entirety. See Inhibition of Androgen Synthesis in Human Testicular and Prostatic Microsomes and in Male Rats by Novel Steroidal Compounds, Endocrinology, Vol. 140, No. 6. Similarly, Nnane et al. also provide for an assay for measuring the activity of 5-reductase by calculating the percentage conversion of tritium-labeled Testosterone (T) to tritium-labeled dihydrotestosterone (DHT) using liquid scintillation spectrometry.

Specific non-limiting examples of anti-androgens useful in the present invention include, but are not limited to, spironolactone (Aldactone, Spiritone; Novo-Spiroton, Spiractin, Verospiron or Berlactone), cyproterone acetate (Androcur, Climen, Diane 35, Ginette 35), flutamide (Eulexin), nilutamide (Anandron, Nilandron), bicalutamide (Casodex) which can be formulated, e.g. as disclosed in U.S. Pat. No. 4,636,505, which is hereby incorporated by reference. Other anti-androgen agents that may be used in the present invention include, but are not limited to, those agents described in WO 02/03912, which is incorporated herein by reference.

The histone deacetylase inhibitor (HDACi) can include, but are not limited to, those HDACi inhibitors described throughout the application. In some embodiments, the HDACi is SAHA, CI-994, MS-275, 3-(1-Methyl-4-phenylacetyl-1H-2-pyrrolyl)-N-hydroxy-2-propenamide (APHA), apicidin, sodium butyrate, (−)-depudecin, scriptaid, sirtinol, trichostatin A and a combination thereof.

In some embodiments, the HDACi is a selective HDACi. For example, in specific embodiments, the Class I selective HDAC inhibitor is, by way of non-limiting example, MGCD-0103 (N-(2-amino-phenyl)-4-[(4-pyridin-3-yl-pyrimidin-2-ylamino)-methyl]-benzamide), MS-275 (N-(2-aminophenyl)-4-(N-(pyridin-3-ylmethoxycarbonyl) aminomethyl) benzamide, SNDX-275), spiruchostatin A, SK7041, CI-994, SK7068 or 6-amino nicotinamides.

In some embodiments, the HDACi is a non-selective HDAC inhibitor. In specific embodiments, the non-selective HDAC inhibitor is, by way of non-limiting example, N'-hydroxy-N-phenyl-octanediamide (suberoylanilide hydroxamic acid, SAHA), pyroxamide, CBHA, trichostatin A (TSA), trichostatin C, salicylihydroxamic acid (SBHA), azelaic bihydroxamic acid (ABHA), azelaic-1-hydroxamate-9-analide (AAHA), depsipeptide, FK228, 6-(3-chlorophenylureido) carpoic hydroxamic acid (3C1-UCHA), oxamflatin, A-161906, scriptaid, PXD-101, LAQ-824, CHAP, MW2796, LBH589 or MW2996.

In some preferred embodiments of the invention, the HDACi is selected from one of the following groups or is a specific compound identified in one of the following groups: The short-chain fatty acids (e.g., butyrate and phenylbutyrate, isovalerate, valproate, 4-phenyl butyrate (4-PBA), phenylbutyrate propionate, butyaramide, isobutyaramide, phenylacetate, 3-bromopropionate, tributyrin, valproic acid, and Pivanex); hydroxamic acids (e.g., the trichostatins such as TSA and TSC, suberoylanilide hydroxamic acid ("SAHA") and its derivatives, Oxamflatin, azelaic biyhydroxamic acid ("ABHA"), azelaic-1-hydroxamate-9-anilide ("AAHA"), suberoyl bishydroxamic acid ("SBHA"), m-carboxycinnamic acid bishydroxamide ("CBHA"), pyrozamide, salicylbishyudoxamic acid, Scriptaid, Pyroxamide, Propenamides, LBH589, CHAP, MY29996, MW2976, and any of the hydroximic acids disclosed in U.S. Pat. Nos. 5,369,108; 5,932,616; 5,5,700,811; 6,087,367; and 6,511,990); epoxyketone-containing cyclic tetrapeptides (e.g., trapoxins, depeudecin, depsipeptide FK228, FR 225497, Apicidin, cyclic tetrapeptide, Apicidin Ia, Apicidin Ib, Apicidin Ic, Apicidin Ia, Apicidin IIb, a cycli tetrapeptide containing a 2-amino-8-oxo-9,10-epoxy-decanoyl moiety, a cyclic peptide without the 2-amino-8-oxo-9,10 epoxy-decanoyl moity, HC-toxin, Chlamydocin, Diheteropeptin, WF-3161, Cyl-1 and Cyl-2); non-epoxyketone-containing cyclic tetrapeptides (e.g., FR901228, Apicidin, cyclic-hydroxamic-acid-containing peptides (CHAPs); benzamides (e.g., MS-275 (MS-27-275), N-acetyldinaline, CI-994, MGCD0103, other benzamide analogs); and other miscellaneous structures (e.g., Savicol, Bacecca, MG98, Depudecin, Organosulfur compounds).

In certain embodiments of the present invention, the histone deacetylase inhibitor and the hormone targeted drug are administered simultaneously or the histone deacetylase inhibitor is administered prior to the administration of the hormone targeted drug.

Another embodiment of the present invention comprises a method of increasing sensitivity of a cancer cell to a hormone therapy comprising the step of administering to the cell a histone deacetylase inhibitor in an effective amount to increase the sensitivity of the cancer cell. More specifically, the cancer cell is a breast cancer cell. The cancer cells can be comprised within a subject in need of treatment thereof.

Still further, the breast cancer cell is estrogen receptor negative and administration of the histone deacetylase inhibitor increases the expression of estrogen receptors in the estrogen receptor negative breast cancer cell, thereby treating the breast cancer. Alternatively, the HDACi increase aromatase expression and/or activity, thus making the tumors or neoplasms more sensitive to aromatase inhibitors in addition to antiestrogens.

In certain embodiments, the prostate cancer cell is androgen receptor negative and the histone deacetylase inhibitor increases the expression of androgen receptors on the androgen receptor negative prostate cancer cell.

Another embodiment of the present invention comprises a method of inhibiting growth of a cell comprising contacting the cell with an aromatase inhibitor and a histone deacetylase inhibitor, each in an effective amount to inhibit growth of the cell. The cell is a cancer cell, more specifically, the cancer cell is refractory. Still further, the cancer cell is estrogen receptor negative. In certain embodiments, the histone deacetylase inhibitor increases the expression of an estrogen receptor on the cell.

In a further embodiment, the contacting step occurs in vitro. Still further, the contacting step can occur in vivo. More specifically, the contacting step occurs in a subject in need thereof.

In particular embodiments, there is a method of inhibiting growth of a cell comprising contacting the cell with an aromatase inhibitor and a histone deacetylase inhibitor, each in an effective amount to inhibit growth of the cell, such as a cancer cell. The cancer cell may be refractory, in certain embodiments. In specific embodiments, the cancer cell is estrogen receptor negative or progesterone receptor negative, for example. In some cases, the histone deacetylase inhibitor increases the expression of an estrogen receptor on the cell. The contacting of methods of the invention may be in vitro or in vivo, and it may occur in a subject in need thereof.

In certain embodiments, there is a method of treating an endocrine-regulated cancer in an individual, comprising administering to an individual in need thereof a therapeutically effective amount of a histone deacetylase inhibitor and a therapeutically effective amount of a hormone targeted drug. In a specific embodiment, the cancer has a resistance to treatment with the hormone targeted drug when the hormone targeted drug is administered in an endocrine therapy that does not include the administration of a histone deacetylase inhibitor. The resistance may be de novo resistance or acquired resistance, in particular embodiments. In some cases, the cancer responds to treatment with the hormone targeted drug when administered in an endocrine therapy that does not include the administration of a histone deacetylase inhibitor.

In specific embodiments, the histone deacetylase inhibitor and the hormone targeted drug act on the cancer synergistically, and/or the histone deacetylase inhibitor and the hormone targeted drug are administered simultaneously or sequentially. For example, in some cases, the histone deacetylase inhibitor and the hormone targeted drug are administered sequentially and the histone deacetylase inhibitor is administered prior to the hormone targeted drug.

In particular embodiments, the endocrine-regulated cancer is breast cancer, prostate cancer, ovarian cancer, or endometrial cancer. The cancer may be estrogen receptor negative, progesterone receptor negative, androgen receptor positive, or androgen receptor negative, in certain aspects. The cancer may be positive or negative for aromatase expression. Furthermore, the hormone targeted drug is an aromatase inhibitor, such as anastrozole, exemestane, letrozole, or combinations thereof, in certain aspects.

In other embodiments, there is a method of treating an endocrine-regulated cancer in an individual, comprising administering a therapeutically effective amount of a histone deacetylase inhibitor and a therapeutically effective amount of a hormone targeted drug to the individual, wherein the method overcomes resistance in the endocrine-regulated cancer to the hormone targeted drug. The resistance in the endocrine-regulated cancer may be de novo resistance or acquired resistance, in certain aspects. The histone deacetylase inhibitor and the hormone targeted drug are administered simultaneously or sequentially, in some embodiments.

In a specific embodiment, the cancer has a resistance to treatment with the hormone targeted drug when the hormone targeted drug is administered in an endocrine therapy that does not include the administration of a histone deacetylase inhibitor. The resistance may be de novo resistance or acquired resistance, in particular embodiments. In some cases, the cancer responds to treatment with the hormone targeted drug when administered in an endocrine therapy that does not include the administration of a histone deacetylase inhibitor.

In specific embodiments, the histone deacetylase inhibitor and the hormone targeted drug act on the cancer synergistically, and/or the histone deacetylase inhibitor and the hormone targeted drug are administered simultaneously or sequentially. For example, in some cases, the histone deacetylase inhibitor and the hormone targeted drug are administered sequentially and the histone deacetylase inhibitor is administered prior to the hormone targeted drug.

In particular embodiments, the endocrine-regulated cancer is breast cancer, prostate cancer, ovarian cancer, or endometrial cancer. The cancer may be estrogen receptor negative, progesterone receptor negative, androgen receptor positive, or androgen receptor negative, in certain aspects. Furthermore, the hormone targeted drug is an aromatase inhibitor, such as anastrozole, exemestane, letrozole, or combinations thereof, in certain aspects.

In other embodiments, there is a method of enhancing a response of an endocrine-regulated cancer in an individual to a hormone targeted drug, comprising administering to an individual in need thereof a therapeutically effective amount of a histone deacetylase inhibitor and a therapeutically effective amount of a hormone targeted drug. In certain embodiments, the histone deacetylase inhibitor and the hormone targeted drug act on the cancer synergistically. In particular cases, the endocrine-regulated cancer has a resistance to the hormone targeted drug, and the resistance may be de novo resistance or acquired resistance, for example. In specific embodiments, the histone deacetylase inhibitor and the hormone targeted drug are administered simultaneously or sequentially, for example the histone deacetylase inhibitor and the hormone targeted drug are administered sequentially and the histone deacetylase inhibitor is administered prior to the hormone targeted drug, in specific cases.

In a specific embodiment, the cancer has a resistance to treatment with the hormone targeted drug when the hormone targeted drug is administered in an endocrine therapy that does not include the administration of a histone deacetylase inhibitor. The resistance may be de novo resistance or acquired resistance, in particular embodiments. In some cases, the cancer responds to treatment with the hormone targeted drug when administered in an endocrine therapy that does not include the administration of a histone deacetylase inhibitor.

In particular embodiments, the endocrine-regulated cancer is breast cancer, prostate cancer, ovarian cancer, or endometrial cancer. The cancer may be estrogen receptor negative, progesterone receptor negative, androgen receptor positive, or androgen receptor negative, in certain aspects. Furthermore, the hormone targeted drug is an aromatase inhibitor, such as anastrozole, exemestane, letrozole, or combinations thereof, in certain aspects.

In particular embodiments, prior to treatment with an HDACi and aromatase inhibitor, it is determined that the breast cancer is estrogen receptor positive. In some embodiments, prior to treatment with an HDACi and aromatase inhibitor, it is determined that the breast cancer is estrogen receptor negative. In some embodiments, prior to treatment with the HDACi and aromatase inhibitor, the breast cancer is determined to be ER−, PR+. In some embodiments, prior to treatment with the HDACi and aromatase inhibitor, the breast cancer is determined to be ER−, PR−, and Her2+. In some embodiments, prior to treatment with the HDACi and aromatase inhibitor, the breast cancer is determined to be ER−, PR− and Her2−.

Also provided herein are methods for assaying a breast cancer cell to determine if the breast cancer cell is ER+ or ER− and providing instructions for treating with an HDACi and aromatase inhibitor based on that determination. Also provided herein are methods for assaying a breast cancer cell to determine if the breast cancer cell is ER−, PR+; ER−, PR−, and Her2+; and/or ER−, PR− and Her2−, and providing instructions for treating with an HDACi and aromatase inhibitor based on that determination.

Also provided herein are methods for determining how to treat a breast cancer patient comprising determining if the breast cancer cell is ER+ or ER−. Also provided herein are methods for determining how to treat a breast cancer patient comprising determining if the breast cancer cell is ER−, PR+; ER−, PR−, and Her2+; and/or ER−, PR− and Her2−. In some preferred embodiments, instructions are provided for treatment of a patient with an HDACi and aromatase inhibitor based on the results of this determination.

Also provided herein are kits comprising reagents to determine whether a cell is estrogen receptor positive and instructions for treatment with an HDACi and aromatase inhibitor. Provided herein are kits comprising reagents to determine whether a cell is estrogen receptor negative and instructions for treatment with an HDACi and aromatase inhibitor. Provided herein are kits comprising reagents to determine whether a cell is ER−, PR+ and instructions for treatment with an HDACi and aromatase inhibitor. Provided herein are kits comprising reagents to determine whether a cell is ER−, PR−, and Her2+ and instructions for treatment with an HDACi and aromatase inhibitor. Provided herein are kits comprising reagents to determine whether a cell is ER−, PR− and Her2− and instructions for treatment with an HDACi and aromatase inhibitor.

In particular embodiments, prior to treatment with an HDACi and anti-androgen, it is determined that the prostate cancer is androgen receptor negative. In some embodiments, prior to treatment with an HDACi and anti-androgen, it is determined that the prostate cancer is androgen receptor positive.

Also provided herein are methods for assaying a prostate cancer cell to determine if the prostate cancer cell is androgen receptor negative or androgen receptor positive and providing instructions for treating with an HDACi and anti-androgen based on that determination. Also provided herein are methods for determining how to treat a prostate cancer patient comprising determining if the prostate cancer cell is androgen receptor negative or androgen receptor positive. In some preferred embodiments, instructions are provided for treatment of a patient with an HDACi and anti-androgen based on the results of this determination.

Also provided herein are kits comprising reagents to determine if a cell is androgen receptor negative and instructions for treatment with an HDACi and anti-androgen. Provided herein are kits comprising reagents to determine whether a cell is androgen receptor positive and instructions for treatment with an HDACi and anti-androgen.

In one embodiment of the invention, there is a method of treating a hormone resistant cancer in a subject having or suspected of having the hormone resistant cancer, comprising the step of administering to the subject an effective amount of a histone deacetylase inhibitor and an aromatase inhibitor. In some embodiments, the histone deacetylase inhibitor is PXD-101. In other embodiments, the histone deacetylase inhibitor is LBH589. In one aspect of the invention, the histone deacetylase inhibitor is FK228. In another aspect, the histone deacetylase inhibitor is MGCD-0103. In a specific embodiment, the histone deacetylase inhibitor is R306465. In one case, the histone deacetylase inhibitor is PCI-24781. In another case, the histone deacetylase inhibitor is SB-939. In an additional embodiment of the invention, the histone deacetylase inhibitor is ITF-2357. In a certain aspect, the histone deacetylase inhibitor is SAHA. In a particular aspect, the histone deacetylase inhibitor is CI-994. In one embodiment, the histone deacetylase inhibitor is MS-275. It is contemplated that any combination of these histone deacetylase inhibitors may be employed in any method of the invention. In certain embodiments of the invention the aromatase inhibitor may be of any kind, but in a specific embodiment the aromatase inhibitor is anastrozole. In another specific embodiment, the aromatase inhibitor is exemestane. In one aspect of the invention, the aromatase inhibitor is letrozole. In another aspect of the invention, the aromatase inhibitor is formestane. In certain cases, the aromatase inhibitor is testolactone. It is contemplated that any one or more aromatase inhibitors may be employed in any method of the invention. In particular embodiments, any combination of one or more of the aromatase inhibitors may be employed with any combination of one or more of the histone deacetylase inhibitors.

In another embodiment of the invention, there is a method of treating a hormone resistant cancer in a subject having or suspected of having the hormone resistant cancer, comprising the step of administering to the subject an effective amount of the following: a histone deacetylase inhibitor; and an aromatase inhibitor. In particular embodiments, the histone deacetylase inhibitor is PXD-101. In other embodiments, the histone deacetylase inhibitor is LBH589. In one aspect of the invention, the histone deacetylase inhibitor is FK228. In another aspect, the histone deacetylase inhibitor is MGCD-0103. In a certain embodiment, the histone deacetylase inhibitor is R306465. In one case, the histone deacetylase inhibitor is PCI-24781. In a particular case, the histone deacetylase inhibitor is SB-939. In an additional embodiment of the invention, the histone deacetylase inhibitor is ITF-2357. In a certain aspect, the histone deacetylase inhibitor is SAHA. In one aspect, the histone deacetylase inhibitor is CI-994. In one embodiment, the histone deacetylase inhibitor is MS-275. It is contemplated that any one or more of these histone deacetylase inhibitors may be employed in any method of the invention. In certain embodiments of the invention the aromatase inhibitor may be of any kind, but in a specific embodiment the aromatase inhibitor is anastrozole. In another specific embodiment, the aromatase inhibitor is exemestane. In certain embodiments of the invention, the aromatase inhibitor is letrozole. In another aspect of the invention, the aromatase inhibitor is formestane. In certain cases, the aromatase inhibitor is testolactone. It is contemplated that any one or more aromatase inhibitors may be employed in any method of the invention. In particular embodiments, any combination of one or more of the aromatase inhibitors may be employed with any combination of one or more of the histone deacetylase inhibitors.

In a certain embodiment of the invention, there is a method of treating a hormone resistant breast cancer in a subject having or suspected of having the hormone resistant breast cancer, comprising the step of administering to the subject an effective amount of the following: a histone deacetylase inhibitor selected from the group consisting of SAHA, CI-994, PXD-101, LBH589, FK228, MGCD-0103, R306465, PCI-24781, SB-939, ITF-2357, and MS-275; and an aromatase inhibitor selected from the group consisting of anastrozole, exemestane, letrozole, formestane, testolactone, and a combination thereof. In certain embodiments of the invention, the histone deacetylase inhibitor is PXD-101. In other embodiments, the histone deacetylase inhibitor is LBH589. In some aspects of the invention, the histone deacetylase inhibitor is FK228. In another aspect, the histone deacetylase inhibitor is MGCD-0103. In a certain embodiment, the histone deacetylase inhibitor is R306465. In one case, the histone deacetylase inhibitor is PCI-24781. In at least one case, the histone deacetylase inhibitor is SB-939. In an additional embodiment of the invention, the histone deacetylase inhibitor is ITF-2357. In a certain aspect, the histone deacetylase inhibitor is SAHA. In one aspect, the histone deacetylase inhibitor is CI-994. In specific embodiments, the histone deacetylase inhibitor is MS-275. It is contemplated that any one or more of these histone deacetylase inhibitors may be employed in any method of the invention. In certain embodiments of the invention the aromatase inhibitor may be of any kind, but in a specific embodiment the aromatase inhibitor is anastrozole. In another specific embodiment, the aromatase inhibitor is exemestane. In certain embodiments of the invention, the aromatase inhibitor is letrozole. In another aspect of the invention, the aromatase inhibitor is formestane. In certain cases, the aromatase inhibitor is testolactone. It is contemplated that any one or more aromatase inhibitors may be employed in any method of the invention. In particular embodiments, any combination of one or more of the aromatase inhibitors may be employed with any combination of one or more of the histone deacetylase inhibitors.

In an additional embodiment of the invention, there is a method of inhibiting growth of a cell comprising contacting the cell with an aromatase inhibitor and a histone deacetylase inhibitor, each in an effective amount to inhibit growth of the cell, wherein the histone deacetylase inhibitor is selected from the group consisting of PXD-101, LBH589, FK228, MGCD-0103, R306465, PCI-24781, SB-939, ITF-2357, SAHA and CI-994 and MS-275. In particular embodiments, the histone deacetylase inhibitor is PXD-101. In other embodiments, the histone deacetylase inhibitor is LBH589. In one aspect of the invention, the histone deacetylase inhibitor is FK228. In another aspect, the histone deacetylase inhibitor is MGCD-0103. In a certain embodiment, the histone deacetylase inhibitor is R306465. In one case, the histone deacetylase inhibitor is PCI-24781. In a particular case, the histone deacetylase inhibitor is SB-939. In an additional embodiment of the invention, the histone deacetylase inhibitor is ITF-2357. In a certain aspect, the histone deacetylase inhibitor is SAHA. In one aspect, the histone deacetylase inhibitor is CI-994. In one embodiment, the histone deacetylase inhibitor is MS-275. It is contemplated that any one or more of these histone deacetylase inhibitors may be employed in any method of the invention. In certain embodiments of the invention the aromatase inhibitor may be of any kind, but in a specific embodiment the aromatase inhibitor is anastrozole. In another specific embodiment, the aromatase inhibitor is exemestane. In certain embodiments of the invention, the aromatase inhibitor is letrozole. In another aspect of the invention, the aromatase inhibitor is formestane. In certain cases, the aromatase inhibitor is testolactone. It is contemplated that any one or more aromatase inhibitors may be employed in any method of the invention. In particular embodiments, any combination of one or more of the aromatase inhibitors may be employed with any combination of one or more of the histone deacetylase inhibitors.

In an additional embodiment of the invention, there is a method of inhibiting growth of a cell comprising contacting the cell with an aromatase inhibitor and a histone deacetylase inhibitor, each in an effective amount to inhibit growth of said cell, wherein the aromatase inhibitor is selected from the group consisting of anastrozole, exemestane, letrozole, formestane, testolactone, and a combination thereof. In particular embodiments, the histone deacetylase inhibitor is PXD-101. In other embodiments, the histone deacetylase inhibitor is LBH589. In one aspect of the invention, the histone deacetylase inhibitor is FK228. In another aspect, the histone deacetylase inhibitor is MGCD-0103. In a certain embodiment, the histone deacetylase inhibitor is R306465. In one case, the histone deacetylase inhibitor is PCI-24781. In a particular case, the histone deacetylase inhibitor is SB-939. In an additional embodiment of the invention, the histone deacetylase inhibitor is ITF-2357. In a certain aspect, the histone deacetylase inhibitor is SAHA. In one aspect, the histone deacetylase inhibitor is CI-994. In one embodiment, the histone deacetylase inhibitor is MS-275. It is contemplated that any one or more of these histone deacetylase inhibitors may be employed in any method of the invention. In certain embodiments of the invention the aromatase inhibitor may be of any kind, but in a specific embodiment the aromatase inhibitor is anastrozole. In another specific embodiment, the aromatase inhibitor is exemestane. In certain embodiments of the invention, the aromatase inhibitor is letrozole. In another aspect of the invention, the aromatase inhibitor is formestane. In certain cases, the aromatase inhibitor is testolactone. It is contemplated that any one or more aromatase inhibitors may be employed in any method of the invention. In particular embodiments, any combination of one or more of the aromatase inhibitors may be employed with any combination of one or more of the histone deacetylase inhibitors.

In one embodiment of the invention, there is a method of treating a hormone resistant cancer in a subject having or suspected of having the hormone resistant cancer, comprising the step of administering to the subject an effective amount of the following: a histone deacetylase inhibitor; and an anti-androgen, wherein the anti-androgen is not a 17alpha-hydroxylase-C17,20-lyase inhibitor or a 5-reductase inhibitor. In a specific embodiment, the hormone resistant cancer is prostate cancer. In another specific embodiment, the histone deacetylase inhibitor is a selective histone deacetylase inhibitor. In a further specific embodiment, the histone deacetylase inhibitor is selected from the group consisting of SAHA, CI-994, PXD-101, LBH589, FK228, MGCD-0103, R306465, PCI-24781, SB-939, ITF-2357, and MS-275. In certain aspects, the anti-androgen is selected from the group consisting of spironolactone (Aldactone, Spiritone; Novo-Spiroton, Spiractin, Verospiron or Berlactone), cyproterone acetate (Androcur, Climen, Diane 35, Ginette 35), flutamide (Eulexin), nilutamide (Anandron, Nilandron), bicalutamide (Casodex) and a combination thereof. In some aspects, the histone deacetylase inhibitor and the anti-androgen are administered simultaneously. In other aspects, the histone deacetylase inhibitor is administered prior to the administration of the anti-androgen. In particular cases, the histone deacetylase inhibitor and the anti-androgen act synergistically. In some embodiments, the hormone resistance is acquired resistance. In particular embodiments, the histone deacetylase inhibitor is PXD-101. In other embodiments, the histone deacetylase inhibitor is LBH589. In one aspect of the invention, the histone deacetylase inhibitor is FK228. In another aspect, the histone deacetylase inhibitor is MGCD-0103. In a certain embodiment, the histone deacetylase inhibitor is R306465. In one case, the histone deacetylase inhibitor is PCI-24781. In a particular case, the histone deacetylase inhibitor is SB-939. In an additional embodiment of the invention, the histone deacetylase inhibitor is ITF-2357. In a certain aspect, the histone deacetylase inhibitor is SAHA. In one aspect, the histone deacetylase inhibitor is CI-994. In one embodiment, the histone deacetylase inhibitor is MS-275. It is contemplated that any one or more of these histone deacetylase inhibitors may be employed in any method of the invention. In certain aspects, the anti-androgen may be of any suitable kind. In specific embodiments, the anti-androgen is spironolactone (Aldactone, Spiritone; Novo-Spiroton, Spiractin, Verospiron or Berlactone). In certain embodiments, the anti-androgen is cyproterone acetate (Androcur, Climen, Diane 35, Ginette 35). In particular embodiments, the anti-androgen is flutamide (Eulexin). In specific cases, the anti-androgen is nilutamide (Anandron, Nilandron). In specific cases, the anti-androgen is bicalutamide (Casodex). In particular embodiments, any combination of one or more of the anti-androgens may be employed with any combination of one or more of the histone deacetylase inhibitors.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1A shows combination of HDACi with tamoxifen inhibits growth of ER− breast cancer cells and FIG. 1B shows effect of MS-275 on growth of letrozole resistant breast cancer cell lines.

FIG. 3A shows that exemplary HDAC is stimulate aromatase activity. FIG. 3B shows that pre-treatment with MS-275 increases aromatase activity of MDA-MB-231 cells in a dose-dependent manner.

FIG. 16 graphically illustrates the distance cells migrated across the open parting during 18 hours with or without various cell treatments in the cell migration assay.

DETAILED DESCRIPTION OF THE INVENTION

I. Definitions

Figure 1A:
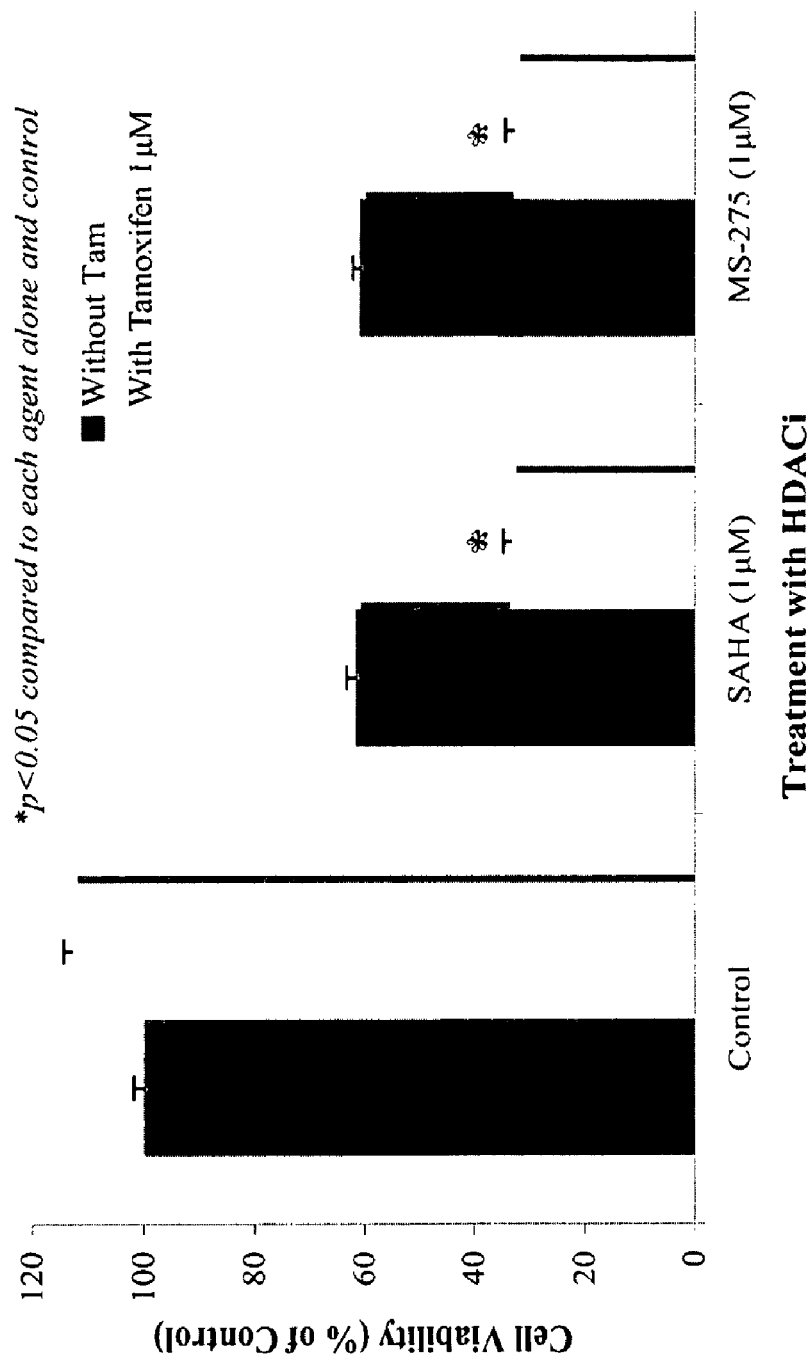
FIG. 1A-FIG. 1B show the effect of HDACi (SAHA or MS-275) on the growth of hormone therapy resistant breast cancer cells lines. In particular.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The term "acquired resistance" as used herein refers to resistance that is acquired after at least one treatment with a given agent. Prior to the at least one treatment, the disorder does not possess a resistance to the agent (and, as such, the disorder responds to the first treatment as would a non-resistant disorder). For example, a hormone-resistant cancer is one that initially responds to at least one treatment of a hormone or endrocrine therapy and thereafter develops a resistance to subsequent treatments of the hormone or endrocrine therapy.

The term "non-androgen responsive" or "androgen resistant" or "androgen negative" refers to a neoplasm that does not utilize an androgen or a derivative thereof or is not sensitive to an androgen or derivative thereof to develop, proliferative and/or metastasize.

The term "de novo resistance" as used herein refers to resistance that exists prior to treatment with a given agent. Therefore, de novo hormone-resistant cancers are resistant to hormone or endocrine therapy prior to the administration of at least one treatment of a hormone or endrocine therapy. In some embodiments, a cancer that is de novo resistant to hormone or endocrine therapy is a cancer that is hormone receptor negative (e.g., estrogen receptor negative or progesterone receptor negative).

The term "effective amount" or "therapeutically effective amount" as used herein is defined as an amount of the agent that will decrease, reduce, inhibit or otherwise abrogate the growth of a neoplasm, induce apoptosis, inhibit angiogenesis of a neoplasm, inhibit metastasis, or induce cytotoxicity in a neoplasm. Thus, an effective amount is an amount sufficient to detectably and repeatedly ameliorate, reduce, minimize or limit the extent of the disease or its symptoms.

The term "disease-free survival" as used herein is defined as a time between the first diagnosis and/or first surgery to treat a cancer patient and a first reoccurrence. For example, a disease-free survival is "low" if the cancer patient has a first reoccurrence within five years after tumor resection, and more specifically, if the cancer patient has less than about 55% disease-free survival over 5 years. For example, a high disease-free survival refers to at least about 55% disease-free survival over 5 years.

The term "endocrine-regulated cancer" as used herein refers to cancers that progress, at least at some stage of their progression, in a manner dependent on the expression of a hormone or a hormone receptor, including, by way of non-limiting example, estrogen, progesterone, and/or the receptors thereof.

The term "HDAC inhibitor" as used herein refers to a compound that has the ability to inhibit histone deacetylase activity. This therapeutic class is able to block angiogenesis and cell cycling, and promote apoptosis and differentiation. HDAC inhibitors both display targeted anticancer activity by themselves and improve the efficacy of existing agents as well as other new targeted therapies.

The term "hormone-resistant cancer" as used herein refers to a cancer that has a decreased or eliminated response to a hormone therapy or endocrine therapy when compared to a non-hormone-resistant cancer. From a biological and clinical standpoint, several patterns of resistance can be distinguished: A) tumors that are inherently insensitive to endocrine receptor (e.g., estrogen receptor) targeting despite endocrine receptor expression (pan-endocrine therapy resistance or de novo resistance); B) tumors that are hormone dependent but resistant to one or more specific endocrine therapies (agent-selective resistance; for example responded to tamoxifen but not aromatase inhibitor); and C) tumors that initially respond to endocrine therapy but subsequently progress (acquired resistance). All types of resistance are included herein. In some embodiments, the hormone-resistant cancer is a cancer that is hormone-resistant prior to the administration of a hormone or endrocine therapy (i.e., it is de novo hormone-resistant). In other embodiments, the hormone-resistant cancer is a cancer that is initially not hormone-resistant, but becomes hormone-resistant after at least one treatment of a hormone or endocrine therapy.

The term "hormone therapy" or "endocrine therapy" as used herein is defined as a treatment pertaining to blocking or removing hormones. The treatment may remove the gland that synthesizes the hormone or the prohormone, block or inhibit hormone synthesis, or prevent or inhibit the hormone from binding to its receptor, or down-regulate or degrade the hormone receptor.

The term "hormone agent" or "hormone targeted drug" is an agent that blocks or inhibits hormone synthesis, prevents or inhibits the hormone from binding to its receptor, or down-regulates or degrades the hormone receptor.

The term "endocrine therapy-resistant" or "hormone resistant" as used herein is defined as a subject receiving an endocrine therapy or hormonal therapy and lacks demonstration of a desired physiological effect, such as a therapeutic benefit, from the administration of the therapy.

The term "estrogen-receptor positive" as used herein refers to cancers that do have estrogen receptors while those breast cancers that do not possess estrogen receptors are "estrogen receptor-negative."

The term "neoplasm" as used herein refers to an abnormal formation of tissue, for example, a tumor. One of skill in the art realizes that a neoplasm encompasses benign tumors and/or malignant tumors. Yet further, as used herein the terms "neoplasm" and "tumor" are interchangeable.

As used herein the term "refractory" means a cancer that does not respond to treatment. The cancer may be resistant at the beginning of treatment or it may become resistant during treatment.

The term "subject" as used herein, is taken to mean any mammalian subject to which a composition of the present invention is administered according to the methods described herein. In a specific embodiment, the methods of the present invention are employed to treat a human subject. Another embodiment includes treating a human subject suffering from a breast neoplasm.

The terms "synergistic" or "synergistically" as used herein refer to two or more compounds providing a therapeutic effect that is greater than the sum of the therapeutic effects of the two compounds provided as therapy alone.

The term "therapeutically effective amount" as used herein refers to an amount that results in an improvement or remediation of the symptoms of the disease or condition.

The term "therapeutic benefit" as used herein refers to anything that promotes or enhances to a significant extent the well-being of the subject with respect to the medical treatment of his condition, which includes treatment of pre-cancer, cancer, and hyperproliferative diseases. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition. In a specific embodiment, a therapeutic benefit refers to reversing de novo hormone therapy-resistance or preventing the patient from acquiring an hormone therapy-resistance

II. Methods of Treatment

In a particular aspect, the present invention provides methods for the treatment of hormone resistant cancers. The present invention relates to a histone deacetylase inhibitor (HDACi) and targeted hormone agents or drugs that, in some embodiments, shows unexpected, potent synergistic anticancer activity. In certain embodiments, the HDACi increases the sensitivity of the cells to the targeted hormone agent, thus, this combination of HDACi and traditional hormone therapy can be used to treat cancers that are typically not treatable with hormone therapy. Thus, the present invention provides a treatment for hormone resistant cancers in a subject, in particular cases.

A. Cancer Types

In certain embodiments, the HDACi and a targeted hormone agent or drug are administered to a cell. Cells that are encompassed by the present invention include, for example, epithelial cancer cells. In some embodiments, the cancer cell is a hormone resistant cancer cell.

1. Breast Cancer

Cells that are encompassed by the present invention include, but are not limited to, breast cells. More specifically, the breast cell is a cancer cell, a non-cancerous cell or a benign hyperplastic cell. A breast cancer cell may include cells that are drug-resistant, primary cancer cells and/or metastatic cancer cells, for example.

In certain aspects, an effective amount of a HDACi and a targeted hormone agent, e.g., an aromatase inhibitor, may be administered to a subject suffering from breast cancer, more specifically, estrogen receptor negative breast cancer (ER−) or hormone resistant breast cancer. In certain embodiments the HDACi increases aromatase expression and/or activity, thus making the tumors or neoplasms more sensitive to aromatase inhibitors in addition to antiestrogens. The effectiveness of the therapy according to the present invention can be determined in the treatment of estrogen cancer by diagnostic methods that are known and used in the art, for example, but not limited to, a mammogram, an ultrasound, a biopsy, etc.

Other embodiments include methods for inhibiting development of breast cancer in a subject at risk, inhibiting breast cancer metastasis in a subject with primary breast cancer, and/or inhibiting breast cancer progression. Also within the scope of the invention is a method of treating benign breast hyperplasia in a human subject afflicted with benign breast hyperplasia comprising administering a HDACi and a targeted hormone agent thereof to the subject in an amount and duration sufficient to result in cell killing or decreases in cell viability.

Still further, other embodiments can include a method of increasing the sensitivity of estrogen negative cancer cells by administering an HDACi. By administering the HDACi to these estrogen negative cancer cells, the HDACi increases expression of estrogen receptors thereby increasing the sensitivity of these cells to hormone therapy. Thus, the combination of HDACi and endocrine therapies or hormonal therapies, e.g., aromatase inhibitors, can be used to inhibit or reduce estrogen negative type cancer cells thereby treating a hormone therapy resistant cancer with standard hormone therapies in combination with HDAC inhibitors.

Another embodiment of the present invention can comprise a method of inhibiting or decreasing cancer cell growth by administering to the cell a HDACi in combination with an aromatase inhibitor. The HDACi increases aromatase expression and/or activity, thus making the tumors or neoplams more sensitive to aromatase inhibitors in addition to antiestrogens, thus inhibiting or decreasing cell growth or proliferation.

Non-limiting examples of endocrine therapies that are contemplated by the present invention include tamoxifen, raloxifene, toremifene or other SERMs (selective estrogen-receptor modulators). Tamoxifen has been the most commonly prescribed drug to treat breast cancer since its approval by the U.S. Food and Drug Administration (FDA) in the 1970s. Tamoxifen is an anti-estrogen and works by competing with the hormone estrogen to bind to estrogen receptors in breast cancer cells. Tamoxifen has been shown to reduce the risk of recurrence of an original cancer and the risk of developing new cancers by working against the effects of estrogen on breast cancer cells. A pharmaceutical composition comprising tamoxifen is generally administered as an oral composition such as a pill or capsule. Tamoxifen belongs to a class of agents known as selective estrogen receptor modulators. These agents display estrogen antagonist activity on some genes and agonist activity on others.

In other specific embodiments, the endocrine therapy comprises goserelin acetate, leuprolide acetate, exemestane, megestrol, toremifene, fulvestrant, a nonsteroidal or a steroidal aromatase inhibitor including, for example, anastrozole, exemestane and letrozole. Fulvestrant has demonstrated an ability to destroy estrogen receptors in breast cancer cells, for example.

2. Prostate Cancer

In certain aspects, an effective amount of a HDACi and a targeted hormone agent, e.g., as anti-androgen, may be administered to a subject suffering from prostate cancer, more specifically, recurrent prostate cancer, more specifically, hormone resistant prostate cancer. The effectiveness of the therapy according to the present invention can be determined in the treatment of prostate cancer by diagnostic methods that are known and used in the art, for example, but not limited to, analysis of prostate specific antigen (PSA), a prostate biopsy, a rectal exam, or analysis of PSA and rectal exam.

Other embodiments include methods for inhibiting development of prostate cancer in a subject at risk, inhibiting prostate cancer metastasis in a subject with primary prostate cancer, and/or inhibiting prostate cancer progression in subjects.

Also within the scope of the invention is a method of treating benign prostate hyperplasia in a human subject afflicted with benign prostate hyperplasia comprising administering a HDACi and a targeted hormone agent thereof to the subject in an amount and duration sufficient to result in cell killing or decreases in cell viability. The levels of prostate specific antigen (PSA) produced by the hyperplastic cells could also be stabilized or reduced upon treatment with a HDACi and a targeted hormone agent.

Still further, other embodiments can include a method of increasing the sensitivity of androgen negative cancer cells by administering an HDACi. By administering the HDACi to these androgen negative cancer cells, the HDACi increases expression of androgen receptors thereby increasing the sensitivity of these cells to hormone therapy. Thus, HDACi and anti-androgens in combination to inhibit or reduce androgen negative type cancer cells thereby treating a hormone therapy resistant cancer with standard hormone therapies in combination with HDAC inhibitors.

Still other embodiments can include a method of increasing the sensitivity of androgen-receptor positive (AR+) cancer cells by administering an HDACi. By administering the HDACi to these AR+ cancer cells, the HDACi down regulates expression of the androgen receptors thereby increasing the sensitivity of these cells to hormone therapy. In some embodiments, the cancer cells are AR+ and the HDACi resensitizes the cells to an anti-androgen.

In further embodiments, anti-androgens are used in combination with HDACi to treat ER− tumors. In some embodiments, the treatment with the anti-androgen renders the cells ER+.

In other embodiments, anti-estrogens, such as tamoxifen, are used in combination with an HDACi described herein to treat lung cancer.

B. HDACi

Inhibitors of histone deacetylase inhibitors induce hyperacetylation of histones that modulate chromatin structure and gene expression. These inhibitors also induce growth arrest, cell differentiation, and apoptosis of tumor cells. Recently it was reported that HDACi can restore the expression of functional ERα to ER− breast cancer cells (Ferguson et al. 2004; Sharma et al. 2006; Yang et al. 2000; Keen et al. 2003). The discovery of recruitment of histone deacetylase (HDAC) enzymes in cancer has provided a rationale for using inhibition of HDAC activity to release transcriptional repression as viable option toward achieving eventual therapeutic benefit (Vigushin et al. 2002). Histone deacetylase inhibitors (HDACis) block deacetylation function, causing cell cycle arrest, differentiation, and/or apoptosis of many tumors (Vigushin et al. 2002). Silencing of genes that affect growth and differentiation has been shown to occur by aberrant DNA methylation in promoter region and by changes in chromatin structure that involve histone deacetylation. Recent studies have established a link between oncogene-mediated suppression of transcription and recruitment of HDAC into nuclear complex. HDACi such as butyric acid (BA), 4-phenylbutyric acid and trichostatin A reverse this suppression by specific inhibition of HDAC activity, leading to histone hyperacetylation, chromatin relaxation, and enhanced transcription.

The HDACs are a family including at least eighteen enzymes, grouped in three classes (Class I, II and III). Class I HDACs include, but are not limited to, HDACs 1, 2, 3, 8 and 11. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7. As used herein, the term "selective HDAC" refers to an HDAC inhibitor that does not substantially interact with all three HDAC classes. The term "Class I Selective HDAC" refers to an HDAC inhibitor that does not substantially interact with Class II or Class III HDACs.

In various embodiments, the HDAC inhibitor is a non-selective HDAC inhibitor. In specific embodiments, the non-selective HDAC inhibitor is, by way of non-limiting example, N'-hydroxy-N-phenyl-octanediamide (suberoylanilide hydroxamic acid, SAHA), pyroxamide, CBHA, trichostatin A (TSA), trichostatin C, salicylihydroxamic acid (SBHA), azelaic bihydroxamic acid (ABHA), azelaic-1-hydroxamate-9-analide (AAHA), depsipeptide, FK228, 6-(3-chlorophenylureido) carpoic hydroxamic acid (3C1-UCHA), oxamflatin, A-161906, scriptaid, PXD-101 (Belinostat or N-hydroxy-3-[3-](phylamino)sulfonyl phenyl]-2-propenamide), LAQ-824, CHAP, MW2796, LBH589 (Panobinostat), CI-994 ("4-acetylamino-N-(2'-aminophenyl)-benzamide"), R306465, ITF2357, PCI-24781, SB-939, or MW2996.

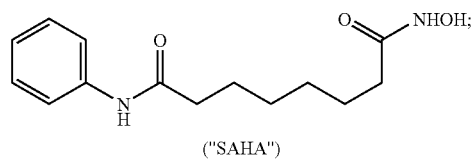

("SAHA")

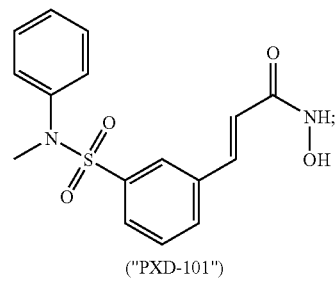

("PXD-101")

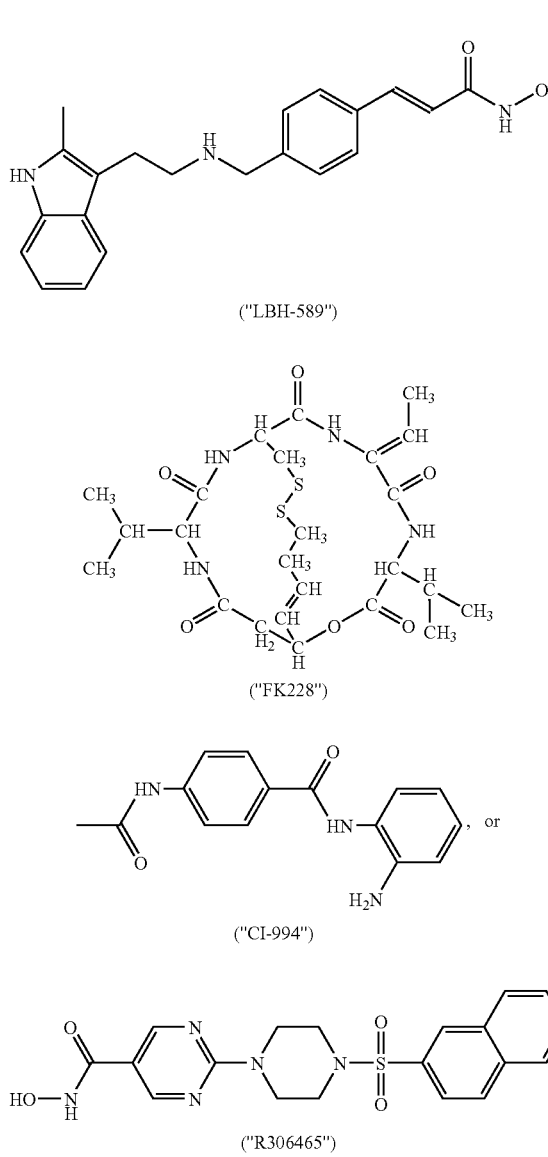

("LBH-589")

("FK228")

("CI-994")

("R306465")

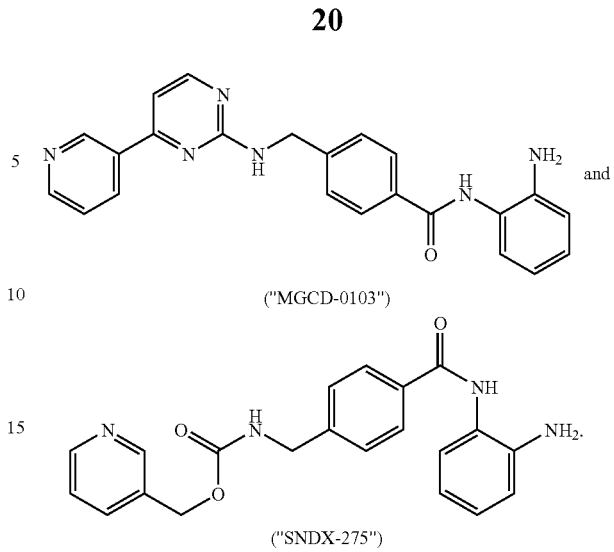

("MGCD-0103")

("SNDX-275")

In certain embodiments, the HDAC inhibitor inhibits at least one of HDAC-1, HDAC-2, HDAC-3, HDAC-8, or HDAC-11. In a specific embodiment, the HDAC inhibitor inhibits HDAC-1. In another embodiment, the HDAC inhibitor inhibits HDAC-2. In yet another embodiment, the HDAC inhibitor inhibits HDAC-3. In another embodiment, the HDAC inhibitor inhibits HDAC-8. In still another embodiment, the HDAC inhibitor inhibits HDAC-11. In other embodiments, the HDAC inhibitor inhibits HDAC-1, HDAC-2, HDAC-3 and HDAC-11.

In specific embodiments of the present invention, the Class I selective HDAC inhibitor is, by way of non-limiting example, MGCD-0103 (N-(2-amino-phenyl)-4-[(4-pyridin-3-yl-pyrimidin-2-ylamino)-methyl]-benzamide), MS-275 (N-(2-aminophenyl)-4-(N-(pyridin-3-ylmethoxycarbonyl) aminomethyl) benzamide, SNDX-275), spiruchostatin A, SK7041, SK7068 and 6-amino nicotinamides.

In various embodiments of the present invention, the HDAC inhibitors are used to increase the sensitivity or to sensitize hormone resistant cancer cells to hormonal therapy. In some embodiments, the HDACi is selected from one of the following groups: The short-chain fatty acids (e.g., butyrate and phenylbutyrate, isovalerate, valproate, 4-phenyl butyrate (4-PBA), phenylbutyrate propionate, butyaramide, isobutyaramide, phenylacetate, 3-bromopropionate, tributyrin, valproic acid, and Pivanex); hydroxamic acids (e.g., the trichostatins such as TSA and TSC, suberoylanilide hydroxamic acid ("SAHA") and its derivatives, Oxamflatin, azelaic biyhydroxamic acid ("ABHA"), azelaic-1-hydroxamate-9-anilide ("AAHA"), suberoyl bishydroxamic acid ("SBHA"), m-carboxycinnamic acid bishydroxamide ("CBHA"), pyrozamide, salicylbishyudoxamic acid, Scriptaid, Pyroxamide, Propenamides, LBH589, CHAP, MY29996, MW2976, and any of the hydroximic acids disclosed in U.S. Pat. Nos. 5,369,108; 5,932,616; 5,5,700,811; 6,087,367; and 6,511,990); epoxyketone-containing cyclic tetrapeptides (e.g., trapoxins, depeudecin, depsipeptide FK228, FR 225497, Apicidin, cyclic tetrapeptide, Apicidin Ia, Apicidin Ib, Apicidin Ic, Apicidin Ia, Apicidin IIb, a cycli tetrapeptide containing a 2-amino-8-oxo-9,10-epoxy-decanoyl moitey, a cyclic peptide without the 2-amino-8-oxo-9,10 epoxy-decanoyl moity, HC-toxin, Chlamydocin, Diheteropeptin, WF-3161, Cyl-1 and Cyl-2); non-epoxyketone-containing cyclic tetrapeptides (e.g, FR901228, Apicidin, cyclic-hydroxamic-acid-containing peptides (CHAPs); benzamides (e.g., MS-275 (MS-27-275, SNDX-275), N-acetyldinaline, CI-994, MGCD0103, other benzamide analogs); and other miscellaneous structures (e.g., Savicol, Bacecca, MG98, Depudecin, Organosulfur compounds).

C. Treatment Regimen

Treatment methods will involve treating an individual with an effective amount of a HDACi and a targeted hormone agent or drug. An effective amount is described, generally, as that amount sufficient to detectably and repeatedly to ameliorate, reduce, minimize or limit the extent of a disease or its symptoms. More specifically, it is envisioned that the treatment with the HDACi and targeted hormone agent will kill cells, inhibit cell growth, inhibit metastasis, decrease tumor size and otherwise reverse or reduce the malignant phenotype of tumor cells.

An effective amount of HDACi and a targeted hormone agent or drug that may be administered to a cell includes a dose of about 0.1 µM to about 100 µM. More specifically, doses of HDACi and a target hormone agent or drug to be administered are from about 0.1 µM to about 1 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

The effective amount or "therapeutically effective amounts" of the HDACi and a targeted hormone agent or drug to be used are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as HDACi and a targeted hormone agent or drug any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

A therapeutically effective amount of HDACi and a targeted hormone agent or drug as a treatment varies depending upon the host treated and the particular mode of administration. However, it is noted that the dosages described in the Examples provided herein provide guidance to the skilled artisan for use in a mammal. For example, in some embodiments it is recognized in the art that dosage by weight in a mouse is usually greater than dosage by weight in a human due to differences in metabolism of at least certain drugs. Therefore, in some cases the dosages described in the Examples may be used as guidance for the maximum dosage that may be utilized for a human, and in certain aspects a certain fold difference less than these dosages is employed in a human. In a specific example, the dosage is an order of magnitude less for a human than a mouse. In certain embodiments, when a combination of HDACi and aromatase inhibitor are employed, the dosages may be the same or less or more than when delivered alone.

With the knowledge of one of skill in the art and the teaching provided herein, dosages for aromatase inhibitors useful in the present invention can be determined. Specific non-limiting examples of doses of aromatase inhibitors include the following: 1 mg of Arimidex administered once a day, 2.5 mg of Femara administered once a day, 25 mg of Teslac administered once a day, and 250 mg Cytadren administered once a day.

Also with the knowledge of one of skill in the art and the teaching provided herein, dosages for anti-androgens useful in the present invention can be determined. Specific non-limiting examples of doses of anti-androgens useful in the present invention include: 25, 50 or 100 mgs Aldactone administered once daily, 300 mgs Androcurus administered once daily, 125 mgs Eulexin administered three times a day, and 150 mgs Nilandron administered twice daily or once daily.

In one embodiment of the invention the dose range of the HDACi and a targeted hormone agent or drug will be about 0.5 mg/kg body weight to about 500 mg/kg body weight. The term "body weight" is applicable when an animal is being treated. When isolated cells are being treated, "body weight" as used herein should read to mean "total cell weight". The term "total weight may be used to apply to both isolated cell and animal treatment. All concentrations and treatment levels are expressed as "body weight" or simply "kg" in this application are also considered to cover the analogous "total cell number" and "total weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for HDACi and targeted hormone agent or drug.

Administration of a HDACi and a targeted hormone agent to a patient or subject will follow general protocols for the administration of chemotherapeutics, taking into account the toxicity, if any. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the HDACi and targeted hormone agent calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion, for example broken into a set of injections, over a set period of time.

According to the present invention, one may treat the cancer by directly injection a tumor with the HDACi and targeted hormone agent. Alternatively, the tumor may be infused or perfused with the composition using any suitable delivery vehicle. Local or regional administration, with respect to the tumor, also is contemplated. More preferably, systemic administration or oral administration may be performed.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes.

In certain embodiments, the tumor being treated may not, at least initially, be resectable. Treatments with a HDACi and a targeted hormone agent may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

III. Combined Cancer Therapy with Other Anticancer Agents

In the context of the present invention, it is contemplated that HDACi and the hormonal therapy thereof may be used in combination with an additional therapeutic agent to more effectively treat the cancer. Anticancer agents may include but are not limited to, radiotherapy, chemotherapy, gene therapy, or immunotherapy that targets cancer/tumor cells.

When an additional therapeutic agent is administered, as long as the dose of the additional therapeutic agent does not exceed previously quoted toxicity levels, the effective amounts of the additional therapeutic agent may simply be defined as that amount effective to inhibit and/or reduce the cancer growth when administered to an animal in combination with the HDACi and the hormonal therapy agents. This may be easily determined by monitoring the animal or patient and measuring those physical and biochemical parameters of health and disease that are indicative of the success of a given treatment. Such methods are routine in animal testing and clinical practice.

To kill cells, induce cell-cycle arrest, inhibit cell growth, inhibit metastasis, inhibit angiogenesis or otherwise reverse or reduce the malignant phenotype of cancer cells, using the methods and compositions of the present invention, one would generally contact a cell with HDACi and the hormonal therapy agent thereof in combination with an additional therapeutic agent. These compositions would be provided in a combined amount effective to inhibit cell growth and/or induce apoptosis in the cell. This process may involve contacting the cells with HDACi and the hormonal therapy agent thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes the HDACi and the hormonal therapy agent thereof and the other includes the additional agent.

Alternatively, treatment with HDACi and the hormonal therapy agent may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TG HDACi and the hormonal therapy agent in combination with an additional therapeutic agent such as anticancer agent will be desired. Various combinations may be employed, where HDACi and the hormonal therapy agent thereof is "A" and the additional therapeutic agent is "B", as exemplified below:

| A/B/A | B/A/B | B/B/A | A/A/B | B/A/A | A/B/B | B/B/ B/A | B/B/ A/B |
|---|---|---|---|---|---|---|---|
| A/A/B/B | A/B/A/B | A/B/B/A | B/B/A/A | B/A/B/A | B/A/ A/B | B/B/ B/A |
| A/A/A/B | B/A/A/A | A/B/A/A | A/A/B/A | A/B/B/B | B/A/ B/B | B/B/ A/B |

A. Chemotherapeutic Agents

In some embodiments of the present invention chemotherapy may be administered, as is typical, in regular cycles. A cycle may involve one dose, after which several days or weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

Chemotherapeutic agents that may be used in combination with the present invention, include, but are not limited to cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, gemcitabien, navelbine, farnesyl-protein tansferase inhibitors, transplatinum, 5-fluorouracil and methotrexate, or any analog or derivative variant of the foregoing.

B. Radiotherapeutic Agents

Radiotherapeutic agents may also be use in combination with the compounds of the present invention in treating a cancer. Such factors that cause DNA damage and have been used extensively include what are commonly known as 7-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapeutic Agents

Immunotherapeutics may also be employed in the present invention in combination with HDACi and the hormonal therapy agent in treating cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and EIB. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK'S. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p61NK4 function by transfection with a plasmid expression vector reduced colony formation by some human cancer cell lines (Okamoto, 1994; Arap, 1995).

Other genes that may be employed according to the present invention include Rb, mda-7, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

E. Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, are contemplated for use in combination with HDACi and a hormonal therapy agent thereof in treating cancer.

F. Surgery

It is further contemplated that a surgical procedure may be employed in the present invention. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

IV. Formulations and Routes for Administration

Where clinical applications are contemplated, it will be necessary to prepare pharmaceutical compositions of HDACi and/or hormone therapy agents, or any additional therapeutic agent disclosed herein in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention in an effective amount may be dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The composition(s) of the present invention may be delivered orally, subcutaneously, nasally, intramuscularly, intraperitoneally, or intratumorally. In some embodiments, local or regional delivery of the composition thereof, alone or in combination with an additional therapeutic agent, to a patient with cancer or pre-cancer conditions will be a very efficient method of delivery to counteract the clinical disease. Similarly, chemo- or radiotherapy may be directed to a particular, affected region of the subject's body. Regional chemotherapy typically involves targeting anticancer agents to the region of the body where the cancer cells or tumor are located. Other examples of delivery of the compounds of the present invention that may be employed include intra-arterial, intracavity, intravesical, intrathecal, intrapleural, and intraperitoneal routes.

Intra-arterial administration is achieved using a catheter that is inserted into an artery to an organ or to an extremity. Typically, a pump is attached to the catheter. Intracavity administration describes when chemotherapeutic drugs are introduced directly into a body cavity such as intravesical (into the bladder), peritoneal (abdominal) cavity, or pleural (chest) cavity. Agents can be given directly via catheter. Intravesical chemotherapy involves a urinary catheter to provide drugs to the bladder, and is thus useful for the treatment of bladder cancer. Intrapleural administration is accomplished using large and small chest catheters, while a Tenkhoff catheter (a catheter specially designed for removing or adding large amounts of fluid from or into the peritoneum) or a catheter with an implanted port is used for intraperitoneal chemotherapy. Because most drugs do not penetrate the bloodlbrain barrier, intrathecal chemotherapy is used to reach cancer cells in the central nervous system. To do this, drugs are administered directly into the cerebrospinal fluid. This method is useful to treat leukemia or cancers that have spread to the spinal cord or brain.

Alternatively, systemic delivery of the chemotherapeutic drugs may be appropriate in certain circumstances, for example, where extensive metastasis has occurred. Intravenous therapy can be implemented in a number of ways, such as by peripheral access or through a vascular access device (VAD). A VAD is a device that includes a catheter, which is placed into a large vein in the arm, chest, or neck. It can be used to administer several drugs simultaneously, for long-term treatment, for continuous infusion, and for drugs that are vesicants, which may produce serious injury to skin or muscle. Various types of vascular access devices are available.

The active compositions of the present invention may include classic pharmaceutical preparations. Administration of these compositions according to the present invention will be via any common route so long as the target tissue is available via that route. This includes but is not limited to, oral, nasal, or buccal routes. Alternatively, administration may be by orthotopic, intradermal, subcutaneous, intramuscular, intraperitoneal or intravenous injection. Such compositions would normally be administered as pharmaceutically acceptable compositions, described supra. The drugs and agents also may be administered parenterally or intraperitoneally. The term "parenteral" is generally used to refer to drugs given intravenously, intramuscularly, or subcutaneously.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation include croscarmellose sodium, hydroxypropyl methylcellulose, iron oxides synthetic), magnesium stearate, microcrystalline cellulose, polyethylene glycol 400, beta-cyclodextran, polysorbate 80, povidone, silicon dioxide, titanium dioxide, and water (purified).

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

V. Kits of the Invention

Any of the compositions described herein may be comprised in a kit. In a non-limiting example, an HDAC inhibitor, an aromatase inhibitor, and/or an anti-androgen may be comprised in a kit. The kits may comprise a suitably aliquoted HDAC inhibitor, an aromatase inhibitor, and/or an anti-androgen, and the components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the HDAC inhibitor, an aromatase inhibitor, and/or an anti-androgen and any other reagent containers in close confinement for commercial sale. Such containers may include injection or blow molded plastic containers into which the desired vials are retained.

Irrespective of the number and/or type of containers, the kits of the invention may also comprise, and/or be packaged with, an instrument for assisting with the injection/administration and/or placement of a component of the kit within the body of an animal or a cell therefrom. Such an instrument may be a syringe, pipette, forceps, and/or any such medically approved delivery vehicle, for example.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Molecular Effects of HDACI on ERA Signaling in ER− Breast Cancer Cells

Methods:
Cell Viability Assessment Using MTT Assay:

MTT assay was performed to measure viability of breast cancer cells after treatment with various test compounds (Sabnis et al. 2005). $IC_{50}$ and $IC_{25}$ values for inhibitors is calculated from the linear regression line of the plot of percentage inhibition versus log inhibitor concentration. These $IC_{50}$ values is used for combination or sequencing studies. The effect of combination or sequence of treatment is determined at $IC_{25}$ of each agent.

Western Immunoblotting for Expression of ERα and Downstream Targets:

The protein extracts from breast cancer (MDA-MB-231 and SKBr3) cells were subjected to western immunoblotting (Sabnis et al. 2005) to measure protein expression of ERα following HDACi treatment. Protein expression of other ER inducible genes such as c-Myc and PgR can also be examined.

Binding Studies:

To confirm affinity of ERα for $E_2$ and AE tamoxifen, binding studies are performed (Long et al. 2002). The ligand used for binding studies is $_3H$-$E_2$. Receptor saturation curve is plotted before fixing the concentration of $_3H$-$E_2$ to be used for competitive binding study with 4-OHT. The saturation curve is plotted with varying concentration of $_3H$-$E_2$ and this enables the inventors to precisely measure the total number of ERαs present inside each cell. The number of receptors is corrected for total number of cells, since treatment with HDACi may have reduce cell number. The binding affinity of PDs is also tested with ERα in wild type MCF-7 cells.

ER Activity Measurement:

To measure the transcriptional activity of re-expressed ERα in the ER− cells ELISA based ERE activity assay are used (Panomics). This assay is performed on nuclear extracts of untreated or HDACi pretreated malignant breast cells. Preparation of nuclear extracts and ERE activity assay is performed as per manufacture's instructions.

Cell Proliferation in Response to Estrogens:

To examine whether pre-treatment with HDACi, restores mitogenic effects of estrogens, non-malignant and malignant breast cells are pre-treated with HDACi followed by treatment with estradiol ($E_2$) and the viability of cells measured by MTT assay.

Figure 1B:
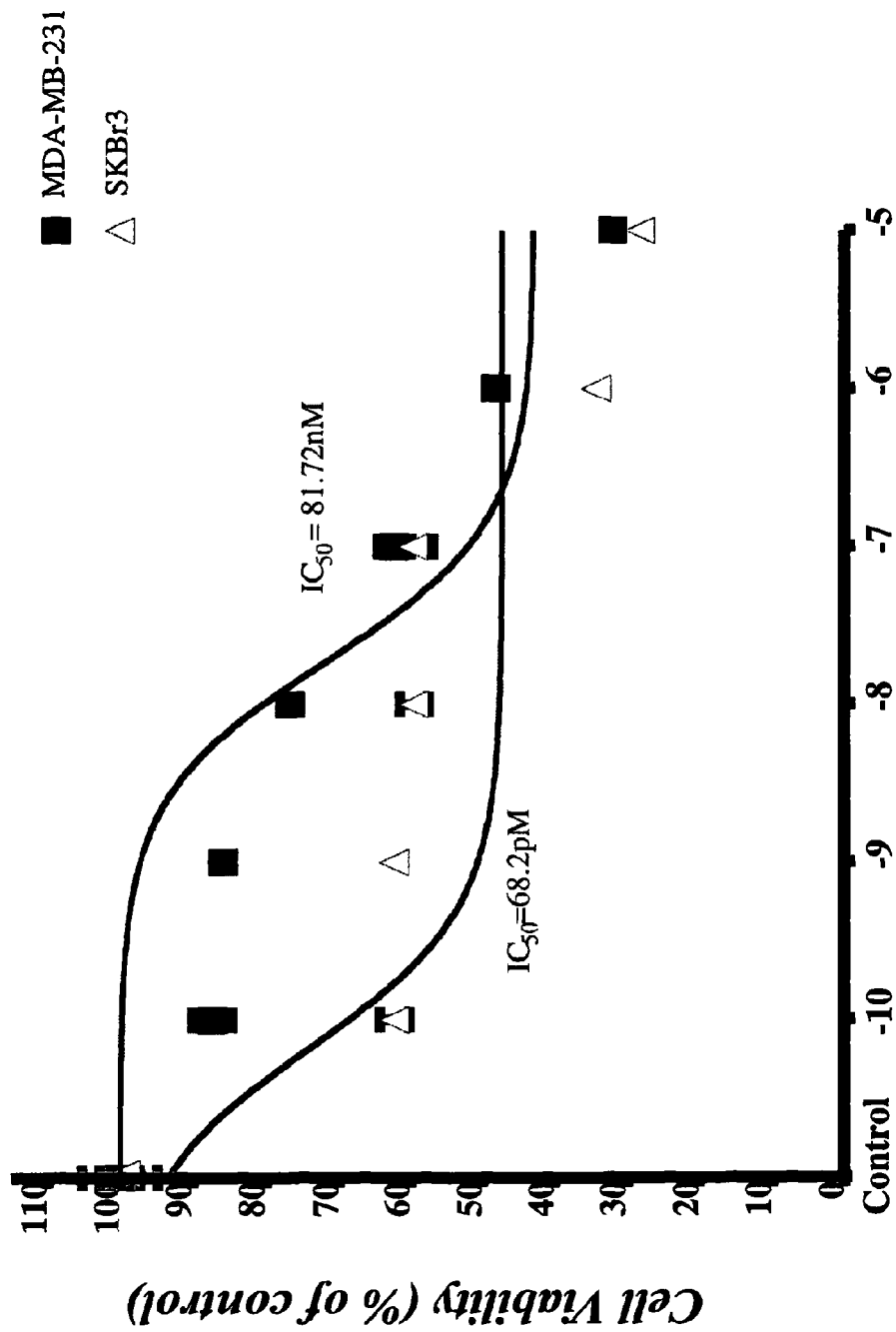

Results:

In this study the inventors have utilized ER– MDA-MB-231 cells. This cell line exhibits no ERα protein expression by western blotting and are refractory to growth inhibitory effects of AEs such as tamoxifen and fulvestrant or AIs such as letrozole, exemestane and anastrozole. In addition, proliferation of these cells was not affected by $E_2$. On the other hand, these cells were significantly inhibited by HDAC is SAHA and MS-275 as shown in FIG. 1A-FIG. 1B. The $IC_{50}$ values for SAHA was 205.1 nM. The $IC_{50}$ value for MS-275 was 81.72 nM.

Furthermore, letrozole alone did not inhibit growth of MDA-MB-231 cells, when combined with MS-275 (0.1 nM) and letrozole was found to synergistically inhibit cell growth in a dose dependent manner ($IC_{50}$=15.43 nM), as shown in FIG. 1C. FIG. 1D shows that letrozole alone did not inhibit growth of MDA-MB-231 cells, however, when combined with SAHA, the combination was found to synergistically inhibit cell growth in a dose dependent manner. Similar results were also obtained in cells that have acquired resistance to letrozole (LTLT-Ca).

In addition, protein expression of ERα was up-regulated 9.9 and 8 fold after treatment with HDAC is SAHA, MS-275 (10 nM) respectively. Although, HDACi BA was not a potent inhibitor of cell growth ($IC_{50}$=20.28 mM), ERα protein expression was up-regulated 15 fold after treatment with 1 μM BA for 24 hours. This restoration of ERα was also associated with restoration of response to tamoxifen. The combination of HDACi with tamoxifen was significantly better than single agent alone ($p<0.01$).

Example 2

Effects on Aromatase Activity

The aromatase activity assay was described by Yue et al. (1997). The expression and activation of aromatase was seen after treatment with HDACi. The basal level of aromatase activity in MDA-MB-231 cells was found to be 3.02 pmoles/μg of protein/hour. When treated with MS-275 (1M) for 24 hours and then incubated with 1β-3H-Androstenedione for 18 hours, the aromatase activity was found to be 15.193 pmoles/μg of protein/hour. This up-regulation of aromatase activity was dose dependent. A similar increase in aromatase activity was observed after pre-treatment with butyric acid. Also, a 24 hour treatment of MDA-MB-231 cells with MS-275 (10 nM), SAHA (10 nM) and BA (1 μM) up-regulated the expression of aromatase by 2.6, 1.77 and 1.2 fold respectively.

Example 3

In Vivo Dose Response Effects of HDACI

Antitumor efficacies of each HDACi are tested in female mice bearing MDA-MB-231 and SKBr3 tumors using in vivo mouse xenograft model. The cell lines used for this study are estrogen independent ER-cell lines. SKBr3 cells. These cells are used for studies with AIs, since these cells have endogenous high levels of aromatase, which is inhibited by AIs. This model simulates advanced and ER-, hormone refractory breast cancer, which is usually associated with mortality of the disease. The xenograft studies are performed as described by Long et al. 2004; Takabatake et al. 2007. Each agent is given at 5 different doses po and sc and effect on the growth of tumors will be examined. During the course of the experiment, tumors are measured weekly with calipers and tumor volume calculated using the formula $[[4/3\pi r1^2 r_2]] (4/3)\pi r_1^2 r_2$ ($r_1 \leq r_2$). After completion of the treatment the animals are euthanized, tumors and uteri are weighed and collected for further analysis. The weight of the uteri is an important bioassay for estrogenic/antiestrogenic activity of the administered agent, since OVX mice have no significant source of estrogen production. The tumors are examined for expression of signaling proteins in the ER pathway as well as activity of ER and downstream targets. The dose of each agent that causes maximum inhibition of tumor growth are used for combination studies.

Example 4

Mouse Xenograft Studies Combination of HDACI with AES/AIS

Experiments are performed to confirm the anti-tumor activity of HDACi and AEs/AIs in mouse xenograft model. The mice receive treatment for a period of at least 8 weeks. The groups of mice ($n \geq 10$) used in the experiment are treated with (but may not be limited to) the following: 1. Vehicle treated control, 2. AE alone (sc 5 times a week), 3. AI alone (sc 5 times a week), 4. HDACi alone, 5. HDACi plus AE, 6. HDACi plus AI, 8. HDACi and AE in sequence, 9. HDACi and AI in sequence. The dose, frequency and route of administration for HDACi are determined from the above experiments. The dose of AEs and AIs are used as determined (Lu et al., 1999) and the drugs will be given sc. During the course of experiment, tumor volumes are measured weekly. After approximately 6-8 weeks, the animals are euthanized, tumors and uteri will be weighed collected for further analysis. Tumor growth rates are calculated to determine significant effect of the treatment on the tumor. The tumors are examined for expression of signaling proteins in the ER pathway as well as activity of ER and downstream targets.

Example 5

In Vivo Metastases Mouse Model

To examine the effects of the above-mentioned combinations and sequences on metastatic spread, a metastasis mouse model is used (Fulton et al. 2006; Walser et al. 2006). Here, MDA-MB-231 cells are injected intravenously into OVX nude mice. All the above-mentioned agents are administered, and after 4 weeks mice are sacrificed and formation of pleural metastasis are assessed.

Example 6

HDAC Inhibitors Sensitize ER-Negative Breast Cancer Cells to Aromatase Inhibitors The ability of HDACi to sensitize exemplary ER-negative breast cancer cells to aromatase inhibitors was characterized. The following exemplary materials and methods were utilized, although one of skill in the art recognizes that alternative but analogous materials and methods may be employed.
Cell Line and Cell Proliferation Assay Exemplary ER negative cell lines (MDA-MB-231) were used. For a cell proliferation assay, $10^4$ cells were plated in a 96 well plate and treated with indicated drugs for 6 days. The medium was replaced after 3 days. On day 7, 500 μg/ml of MTT solution was added to each well and cells incubated for 3 hours. The tetrazolium dye trapped inside the mitochondria of the cells was dissolved in DMSO and the absorbance was measured at 560 nm.

Western Immunoblotting

Expression of ER and Aromatase proteins was examined by Western blotting. β-actin was used as a loading control.

Radiometric $^3$H2O Release Assay for Aromatase Activity 150,000 cells were plated in IMEM without PR with 5% steroid free serum, 1% penicillin-streptomycin and 750 µg/ml G418. Next day the cells were incubated with 0.5 µCi of [1β$^3$H] androstenedione (Specific activity 23.5 Ci/mmole) in 1 ml of media containing 1% charcoal stripped serum for 18 hours. The medium was then collected and treated with TCA (trichloroacetic acid) to precipitate proteins. The residual steroids in the medium were extracted and removed with chloroform and further treated with a 2.5% charcoal suspension. The $^3$H2O in the supernatant was measured using a scintillation counter. In this assay $^3$H2O is released during conversion of [1β$^3$H] Δ4A to estrone, catalyzed by the enzyme aromatase. For pre-treatment studies, cells were plated as described above and then next day pre-treated with indicated agent for 24 hours before incubating with [1β$^3$H] Δ4A for 18 hours. The activity of the enzyme is corrected for protein concentration in the cells plated and treated.

Statistics

ANOVA was performed for multiple comparisons, all comparisons are two sided and p of less than 0.05 was considered statistically significant.

The IC$_{50}$ values of HDAC inhibitors in various cell lines is provided in Table 1 below.

TABLE 1

IC$_{50}$ values for inhibition of ER-cell proliferation

| Compound | MDA-MB-231 | Hs 578T | SKBr3 |
|---|---|---|---|
| Her-2 Status | − | + | ++++ |
| SAHA | 205.10 nM | 16.88 nM | 80.72 nM |
| MS-275 | 81.72 nM | 28.11 nM | 68.2 pM |
| BA | 2028 mM | 67.91 mM | 17.17 µM |
| CJ-994 | 97.79 µM | 122.22 nM | 8.523 µM |

Figure 2:
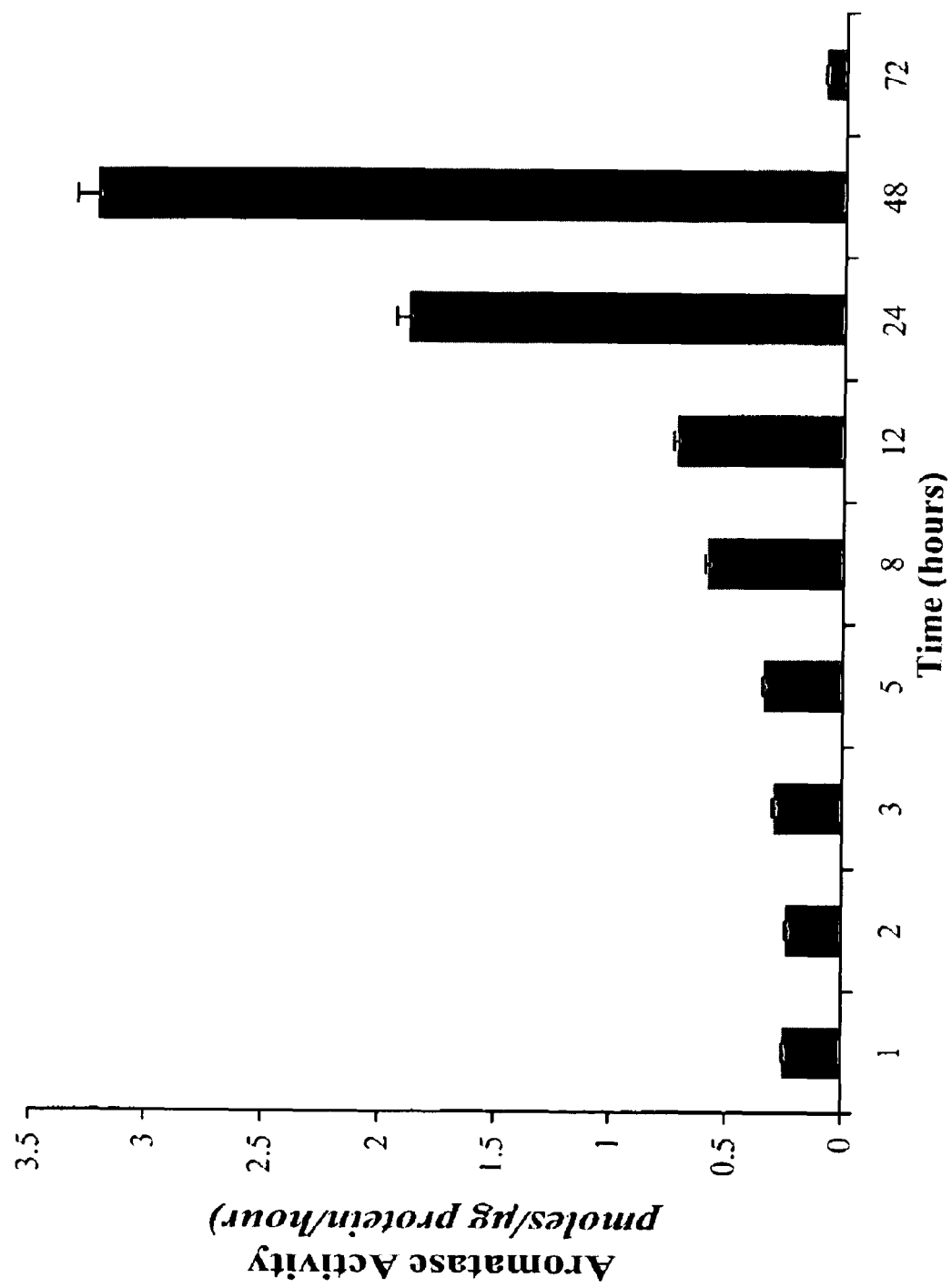
FIG. 2 shows the detectable level of aromatase activity in untreated MDA-MB-231 cells.
Figure 3:
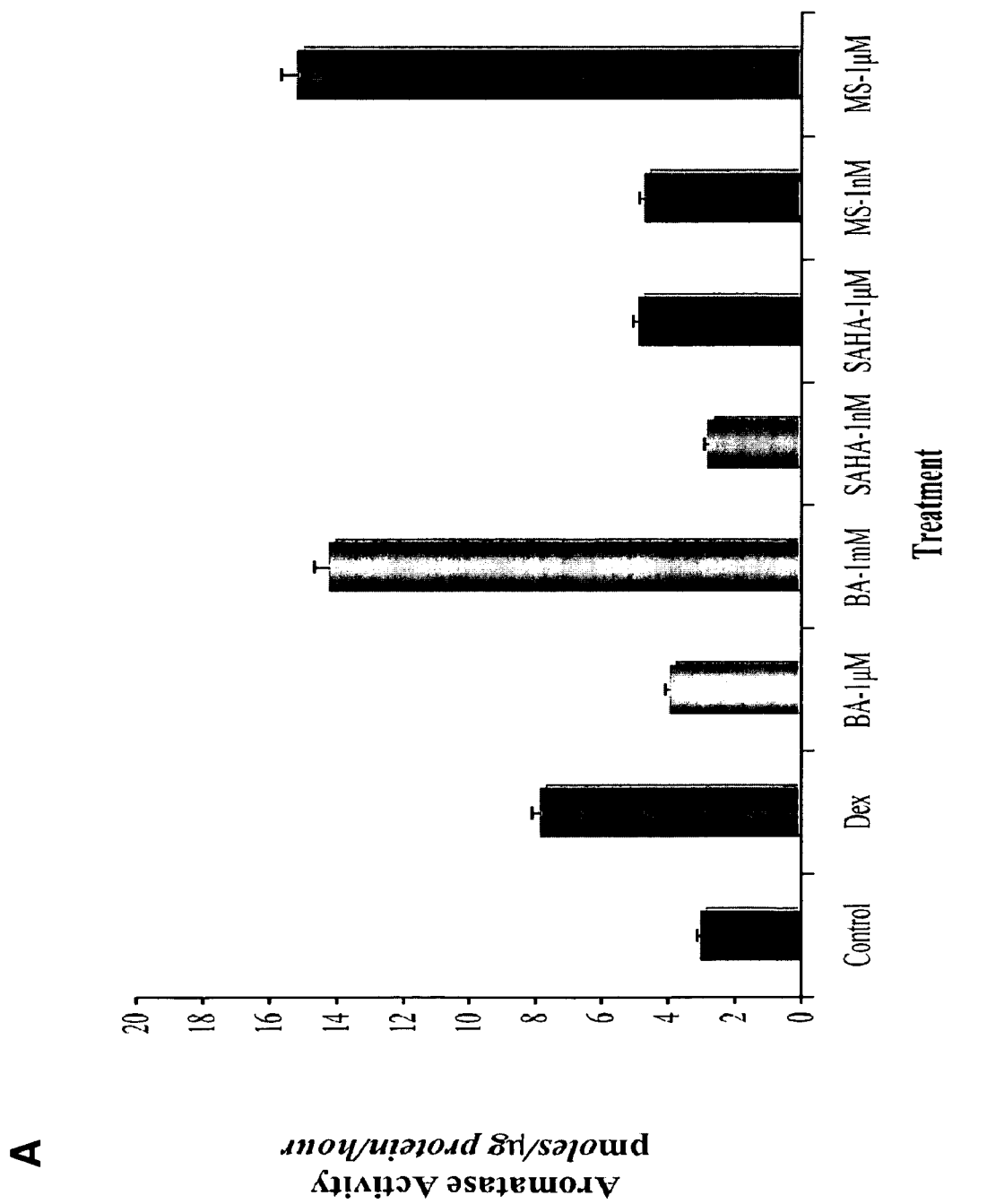
FIGS. 3A-3B show the effect of HDAC on aromatase activity.
Figure 3:
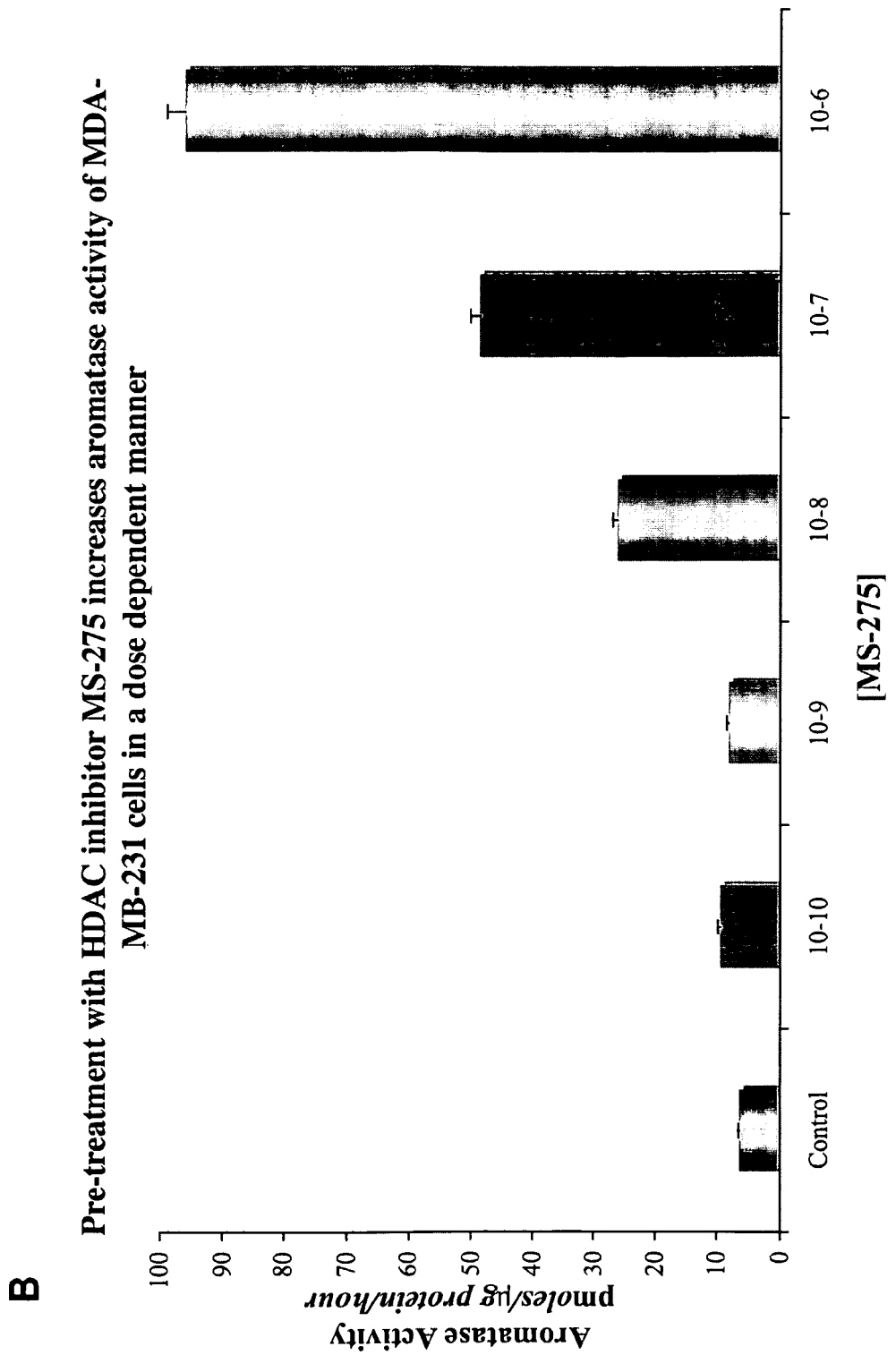
Figure 4:
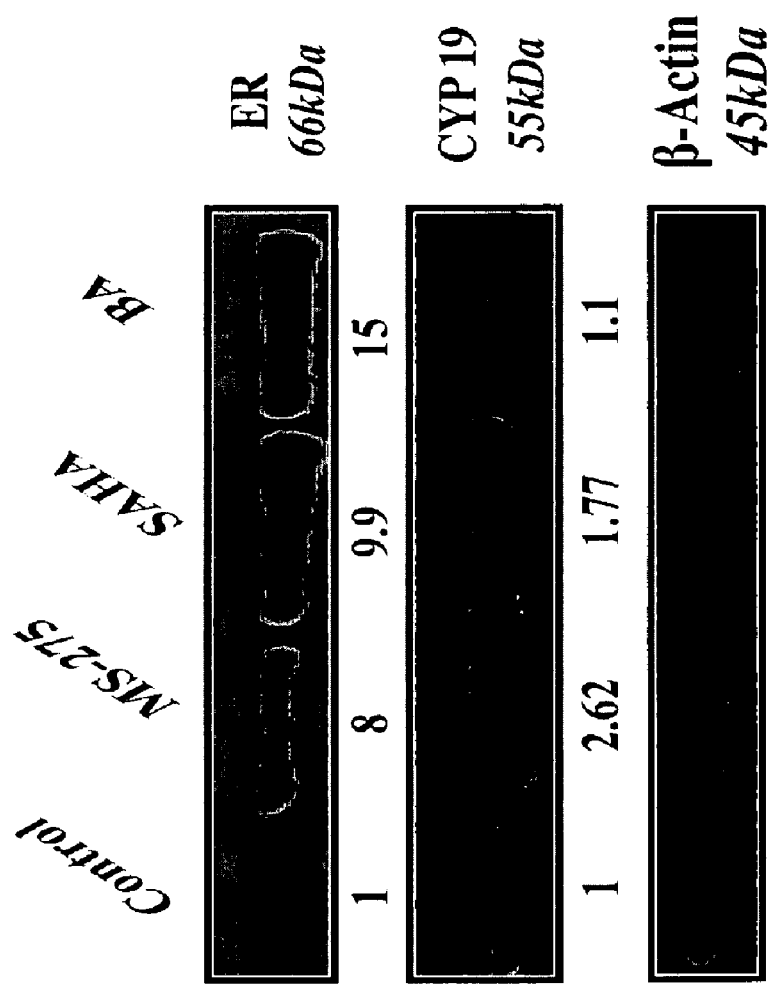
FIG. 4 demonstrates that HDAC inhibitors upregulate ER and aromatase (CYP19) protein expression.
Figure 5:
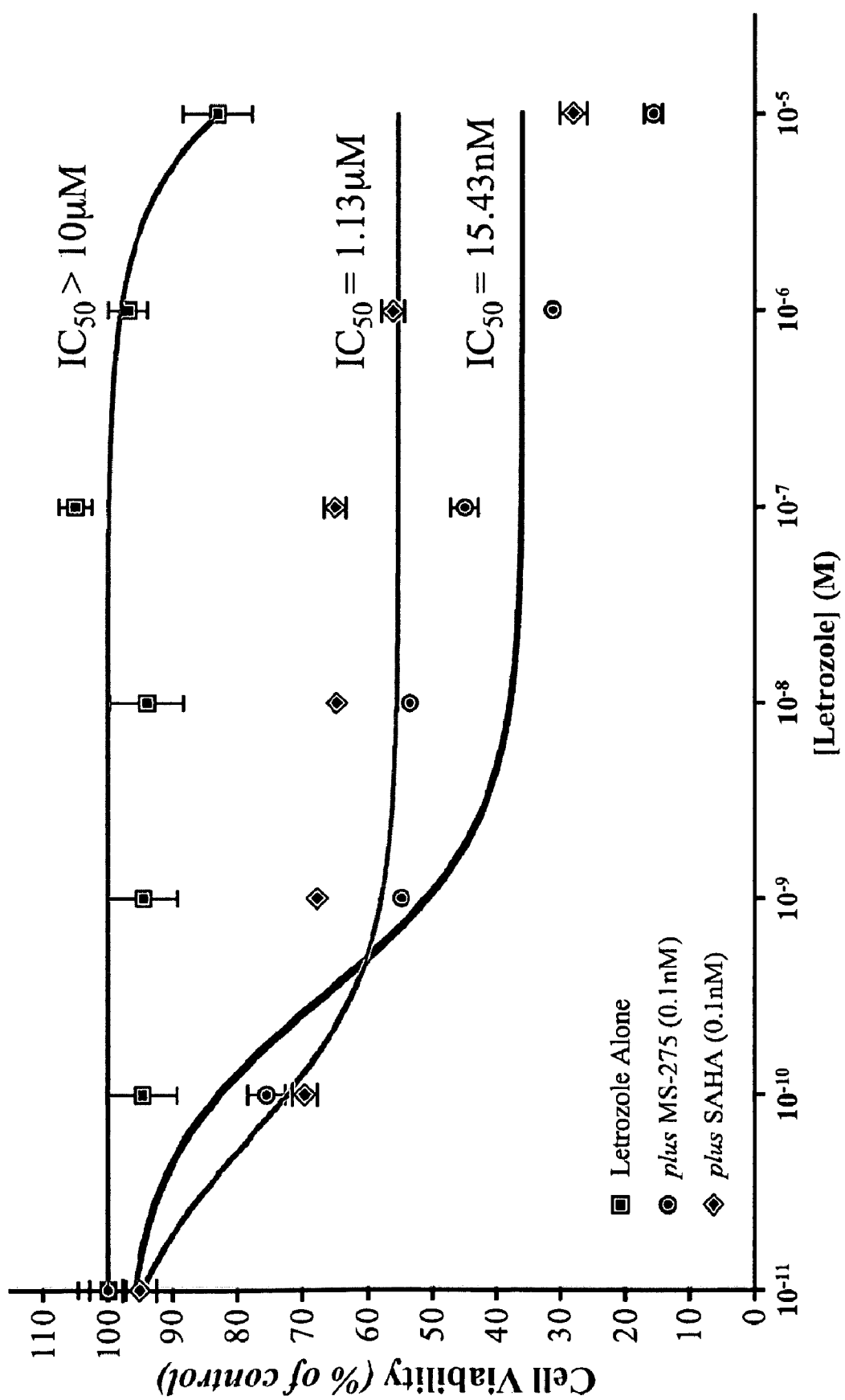
FIG. 5 shows cell viability following delivery of a combination of letrozole with HDACi (MS-275 or SAHA).

It is demonstrated that the exemplary MDA-MB-231 cells are hormone refractory and ER-negative, but they have detectable levels of basal aromatase activity (FIG. 2). Also, the growth of the MDA-MB-231 cells is inhibited by HDAC inhibitors (SAHA, MS-275 and BA) in a dose dependent manner. Furthermore, HDAC inhibitors up-regulate ER and aromatase protein expression after 24 hour treatment (FIG. 4). The aromatase activity is upregulated by HDAC inhibitors SAHA, MS-275 and BA in a dose dependent manner (FIG. 3A). FIG. 3B shows that pre-treatment with MS-275 increases aromatase activity of MDA-MB-231 cells in a dose-dependent manner. Finally, when combined with HDACi SAHA or MS-275, letrozole inhibits the growth of ER-negative MDA-MB-231 cells in a dose dependent manner with IC$_{50}$ values of 1.13 µM and 15.43 nM respectively (FIG. 5).

Therefore, histone deacetylase inhibitors can upregulate ER and aromatase protein expression and upregulate aromatase activity and sensitize ER negative breast cancer cells to endocrine therapy. The combination of AEs or AIs with HDAC inhibitors represents a new strategy for the treatment of cancer, including ER-negative breast cancers that otherwise are treated with chemotherapy.

Example 7

Upregulation of ERA and Aromatase by HDACI MS-275 in an ER Negative Breast Cancer Xenograft Model The present example concerns the effects of MS-275 (which may also be referred to as SNDX-275/entinostat) in an exemplary ER negative breast cancer xenograft model. The exemplary cell line MDA-MB-231 was used.

The tumors of MDA-MB-231 cells were grown in female ovariectomized nude mice. Sub-confluent cells were collected into Citric Saline, centrifuged and resuspended in Matrigel (10 mg/mL) at ~2.5×10$^7$ cells/mL. Each mouse received subcutaneous inoculations in two sites per flank with 100 µL of cell suspension. Mice were then injected subcutaneously daily with 0.3% HPC in 0.9% NaCl (vehicle) until the tumors reached a measurable size (~150 mm$^3$). At this point the mice were grouped such that the starting tumor volumes were not statistically different across the groups. The mice were injected with indicated agents (5×weekly) for indicated time. The tumors were measured weekly with calipers and the tumor volumes were calculated using the formula (4/3)πr$_1$$^2$r$_2$ (r$_1$≦r$_2$).

Expression of ER and aromatase proteins was examined by Western blotting. β-actin was used as a loading control. The radiometric $^3$H2O release assay for aromatase activity was performed as follows: the tumors were homogenized using ice-cold DPBS and the homogenate was used for the aromatase assay. $^3$H2O release assay was performed using [1β$^3$H] androstenedione (Specific activity 23.5 Ci/mmole). The activity of the enzyme is corrected for protein concentration in the tumor homogenates.

ANOVA was performed for multiple comparisons, all comparisons are two sided and p value of less than 0.05 was considered statistically significant.

Figure 6:
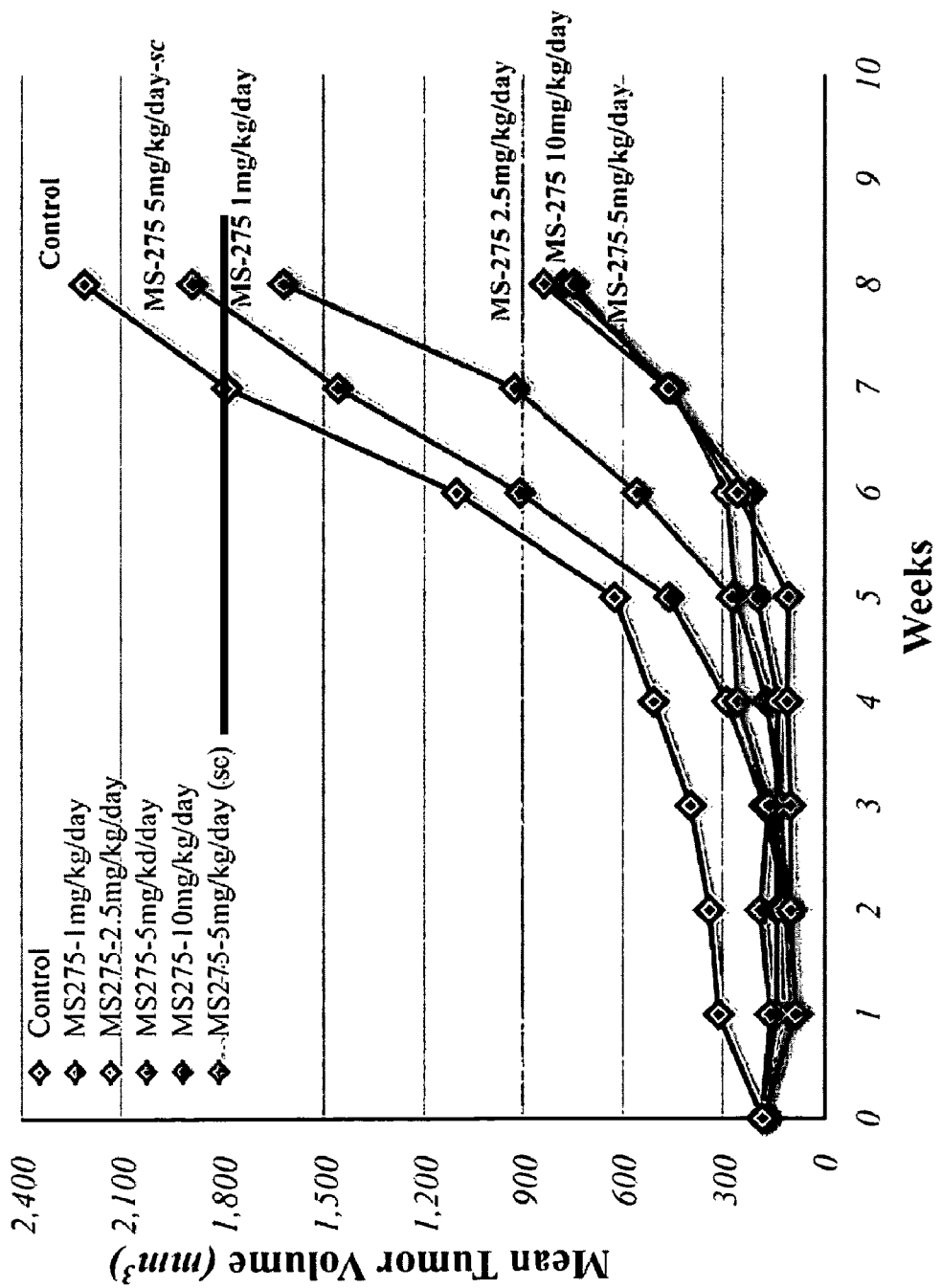
FIG. 6 demonstrates dose-dependent inhibition by MS-275 of the growth of breast cancer xenografts in mice (derived from ER− MDA-MB-231 cells).
Figure 7:
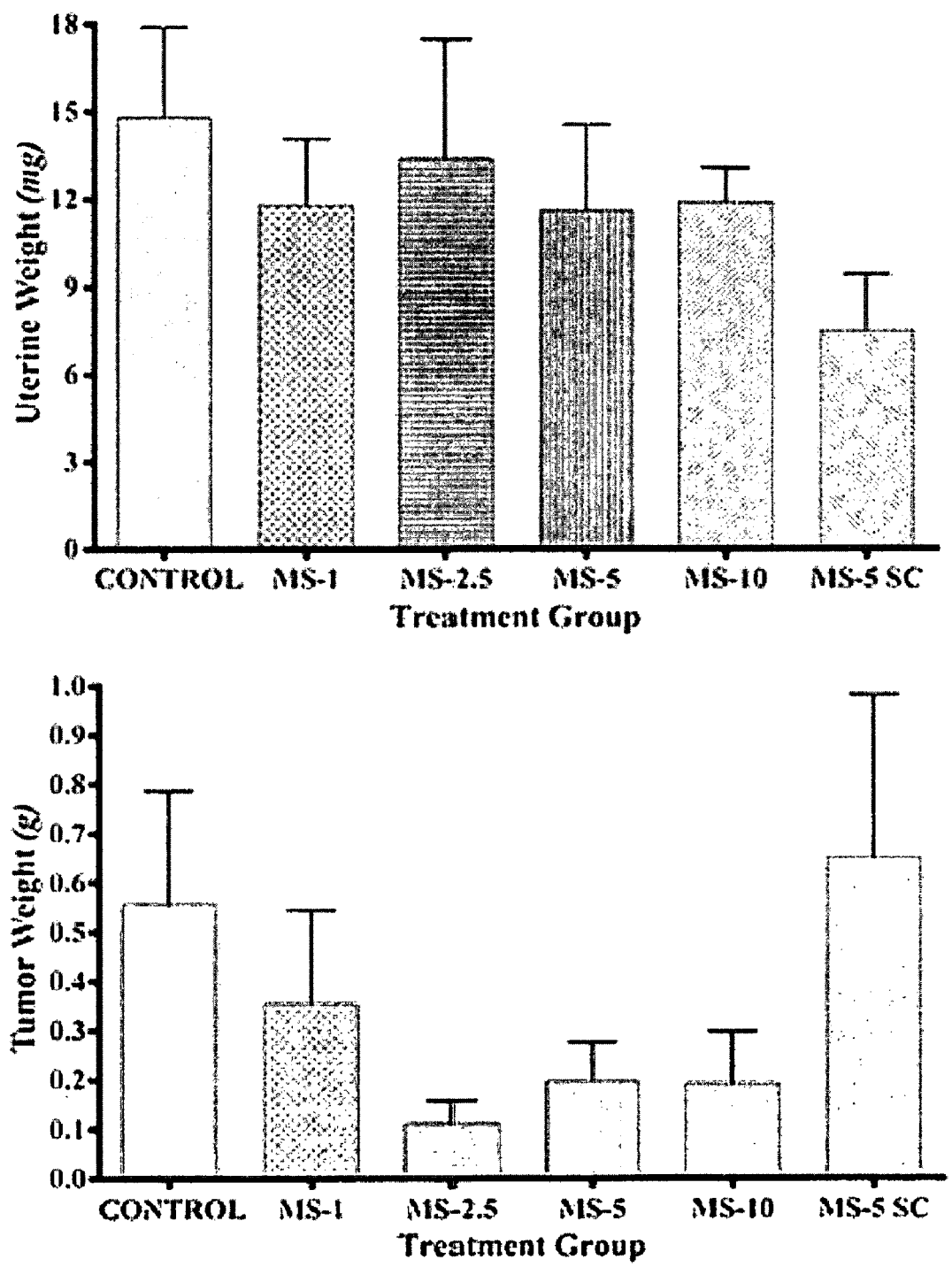
FIG. 7 illustrates the effect of MS-275 on tumor and uterine weights of MDA-MB-231 xenograft-bearing mice.
Figure 8A:
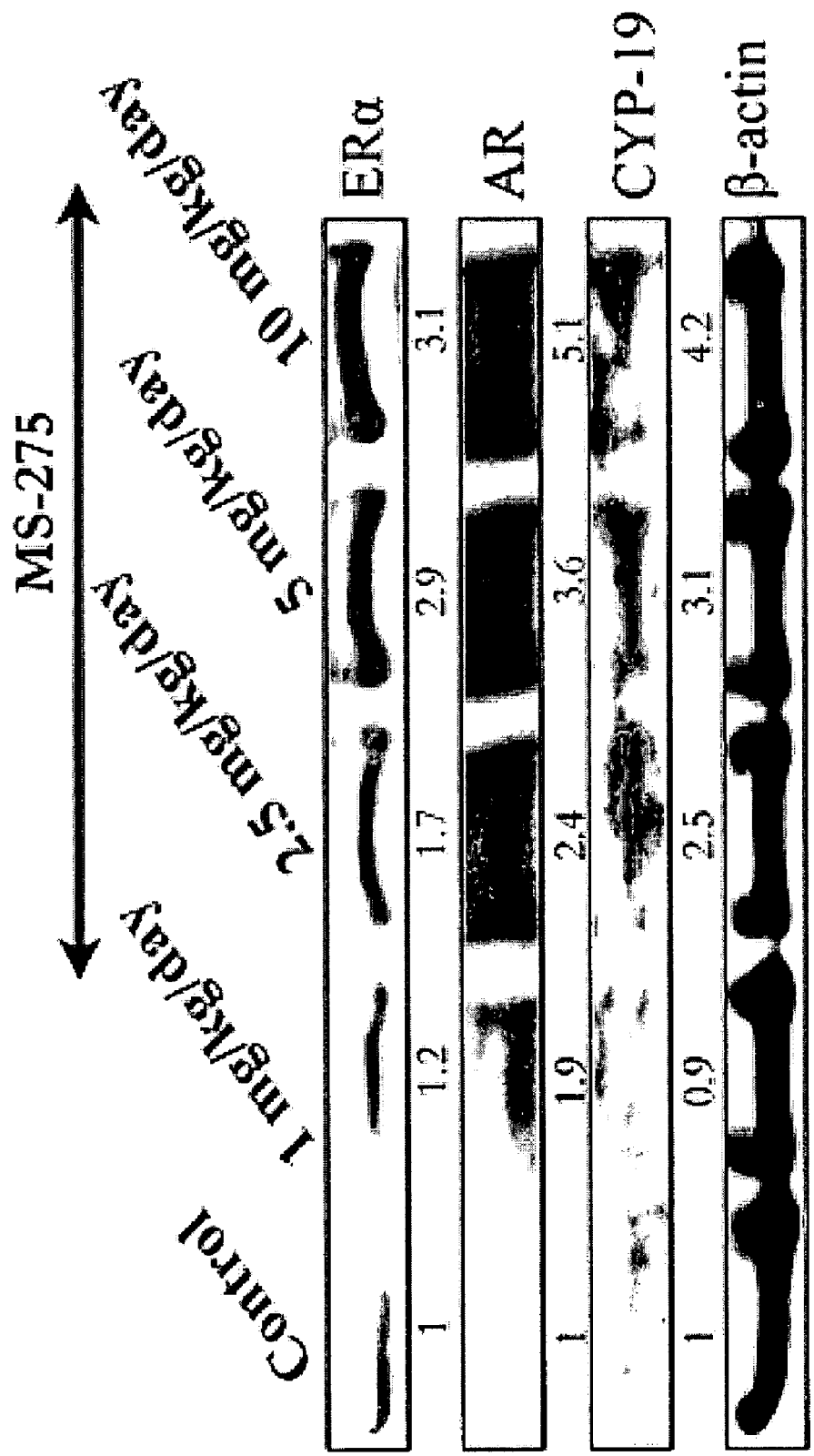
FIG. 8A shows that MS-275 upregulates tumor ER, AR, and aromatase (CYP19) expression in a dose-dependent manner.
Figure 8B:
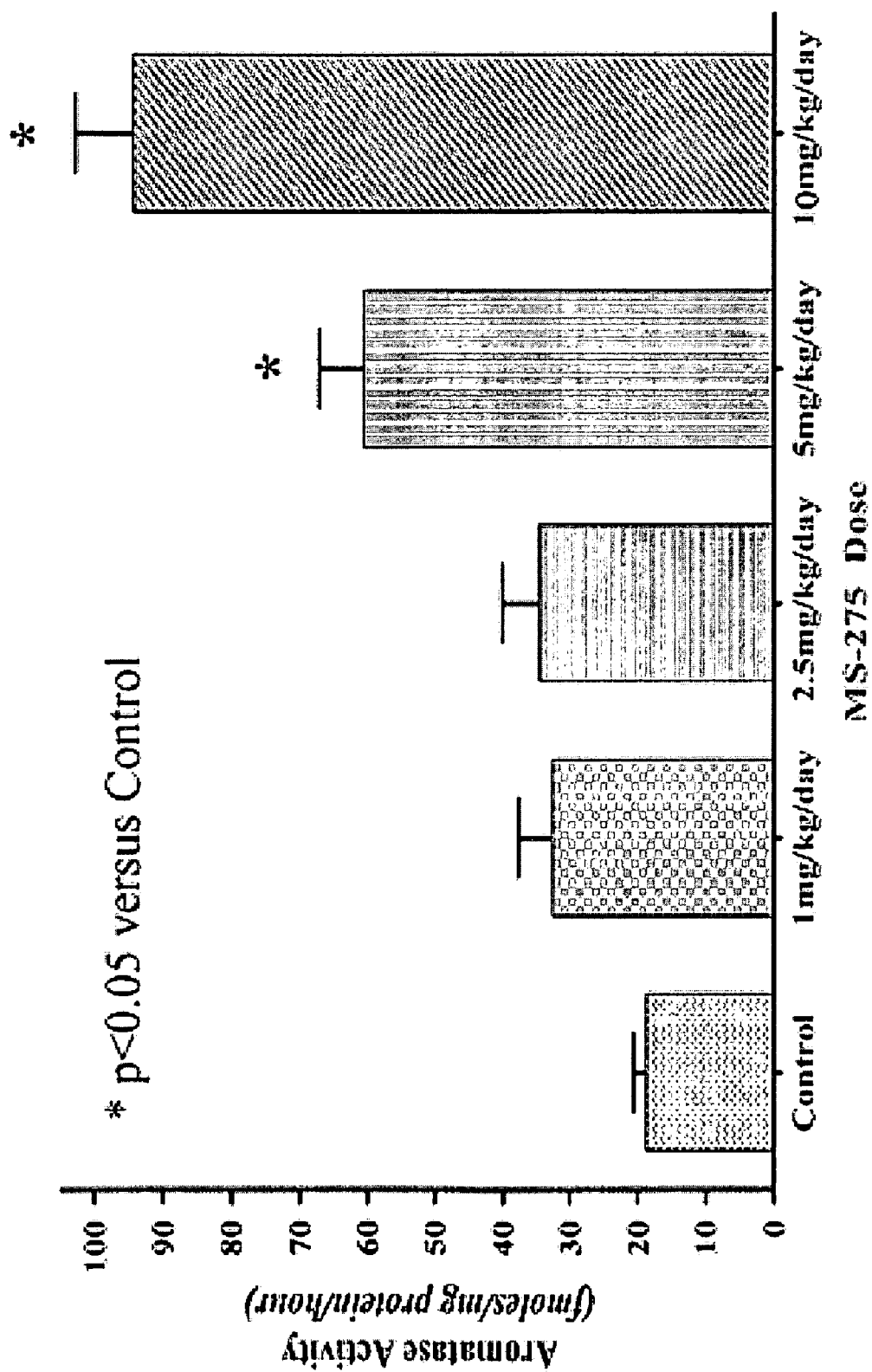
FIG. 8B shows that MS-275 increases aromatase activity in a dose-dependent manner.

As shown in FIG. 6, MS-275 inhibits growth of MDA-MB-231 xenografts in a dose dependent manner. In FIG. 7, the effect of MS-275 on tumor and uterus weights of the mice. FIGS. 8A-8B provide demonstration that MS-275 upregulates tumor ER, aromatase expression, and aromatase activity.

Therefore, the data indicates that MS-275 inhibits growth of MDA-MB-231 xenografts and also upregulates expression of ERα, aromatase and androgen receptor expression in a dose dependent manner. It was also determined that MS-275 is more effective when given orally. MS-275 does not affect the uterine weight by itself, indicating no potential estrogenic or antiestrogenic effects. MS-275 upregulates intra-tumoral aromatase activity. MS-275/SNDX-275/entinostat renders ER negative tumors responsive to endocrine therapy, in particular embodiments of the invention.

Example 8

Combination Therapy with MS-275 and Letrozole for Cancer

Figure 9:
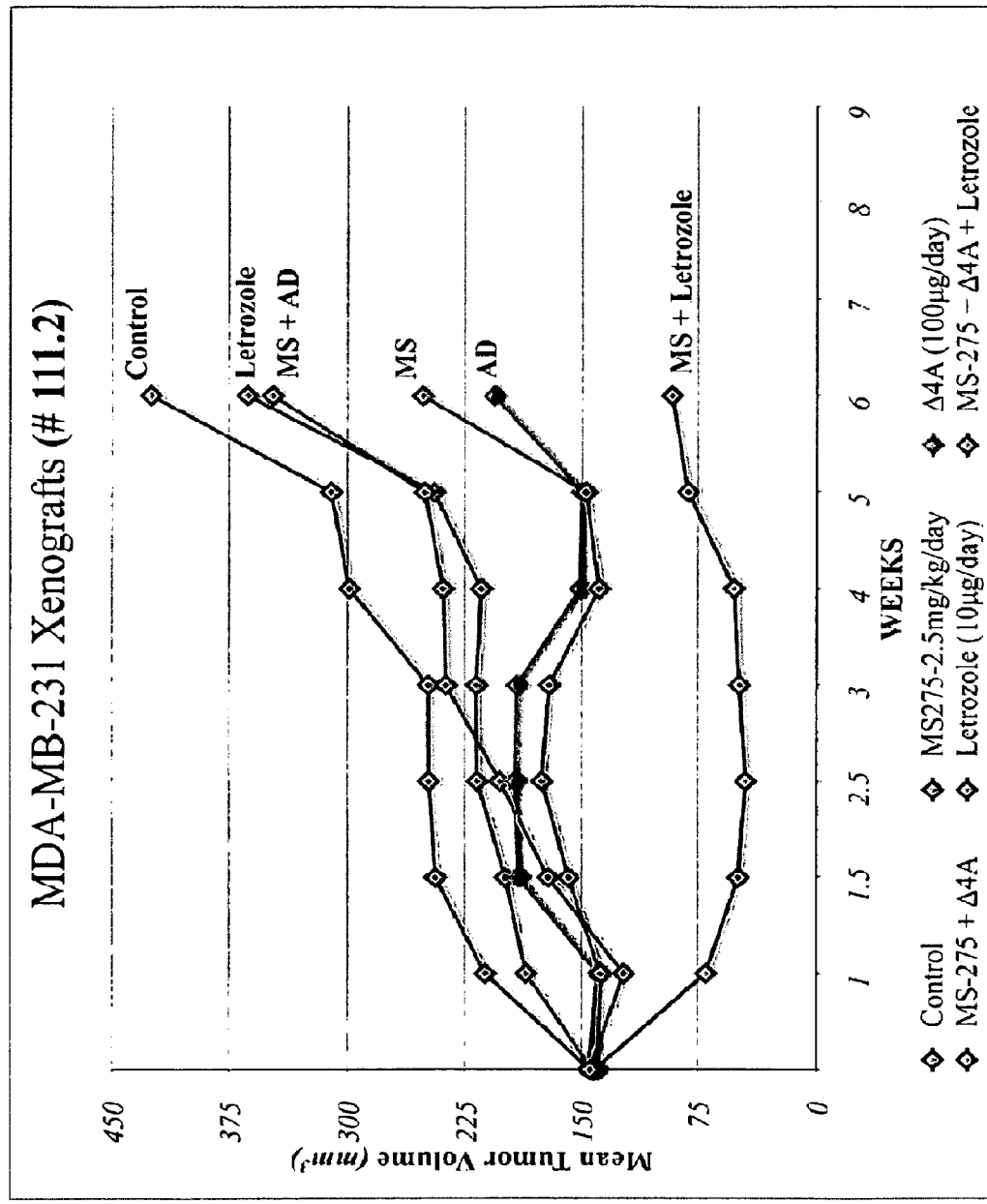
FIGS. 9A-9B demonstrate the effect on tumor volume of singular and combination therapy for MS-275 and letrozole in MDA-MB-231 xenograft-bearing mice.
Figure 9:
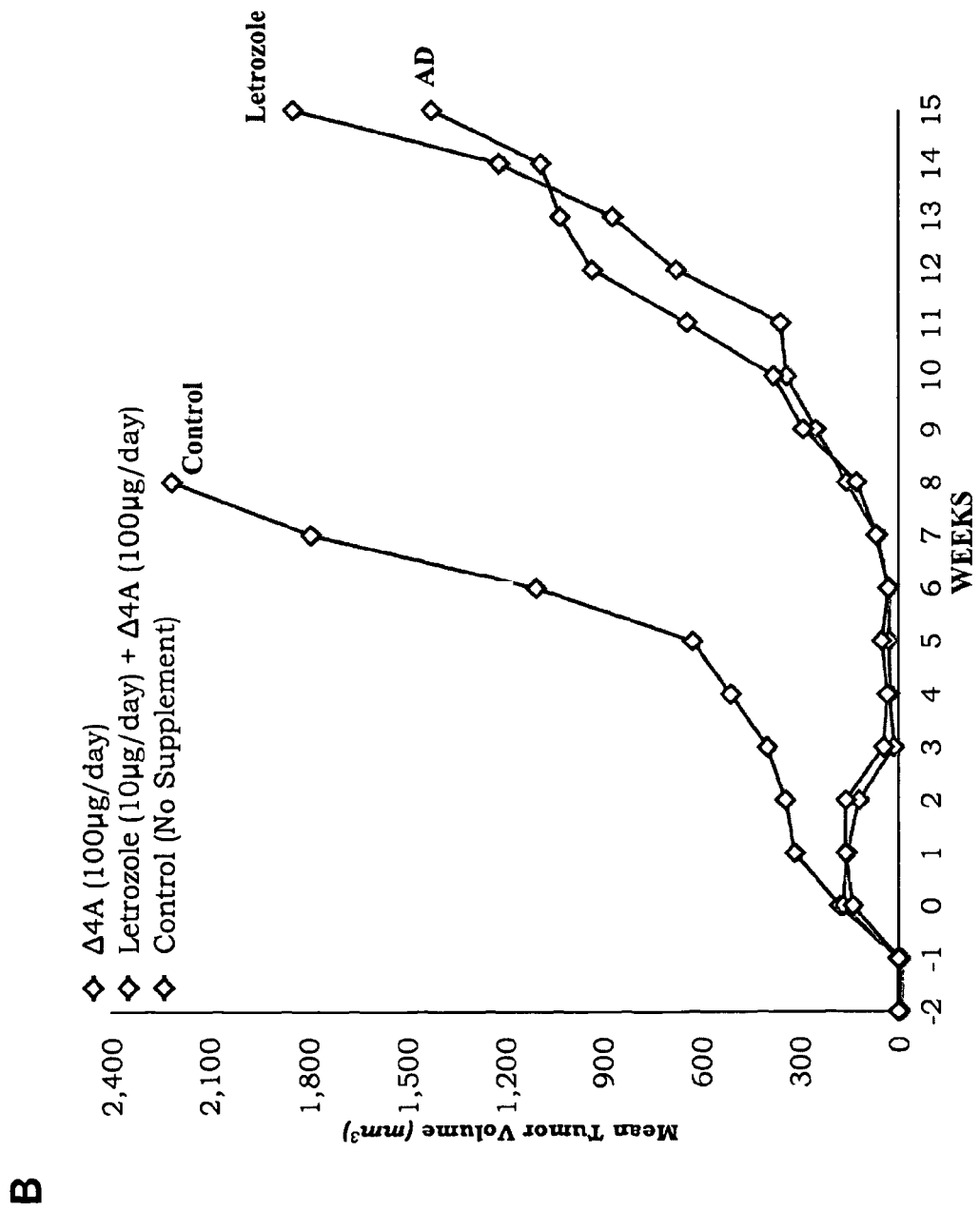

Combination therapy utilizing the exemplary HDAC inhibitor MS-275 and the exemplary aromatase inhibitor letrozole was investigated. MDA-MB-231 xenografts were grown in ovariectomized female nude mice. Mice were inoculated with 2.5×10$^6$ cells per site subcutaneously. When the tumors reached a measurable size ~150 mm$^3$, the mice were grouped into 6 groups (n=10), such that the mean tumor volumes across the groups was not statistically different (p=0.99). The mice were administered androstenedione ($\Delta^4$A) (100 µg/day), Δ4A plus letrozole (10 µg/day), MS-275 (2.5 mg/kg/day), MS-275 plus $\Delta^4$A, MS-275 plus A$^4$A plus letrozole or vehicle. The mice were treated 5 times a week with MS-275 orally and letrozole and $\Delta^4$A sc. The tumors were measured every week with calipers and the tumor volumes were calculated using the formula, $4/3 \, \pi r_1^2 r_2$. FIG. 9A-9B demonstrate the effect on tumor volume of singular and combination therapy for MS-275 and letrozole in MDA-MB-231 xenograft mice.

Example 9

Combination Therapy with MS-275 and Letrozole for Cell Migration Assay

Figure 10:
FIG. 10 is an exemplary cell migration assay in control MDA-MB-231 cells without treatment.
Figure 10:
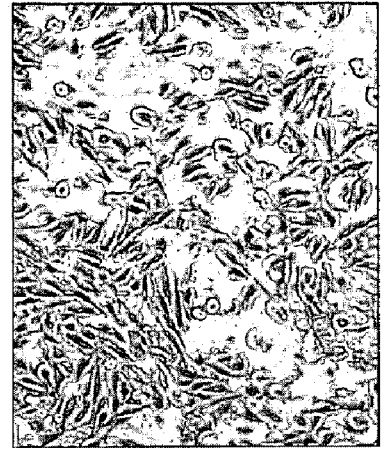
Figure 10:
Figure 10:
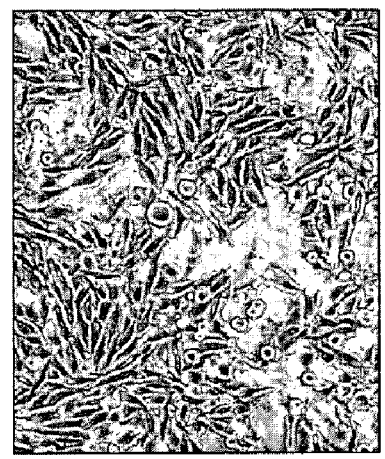
Figure 10:
Figure 10:
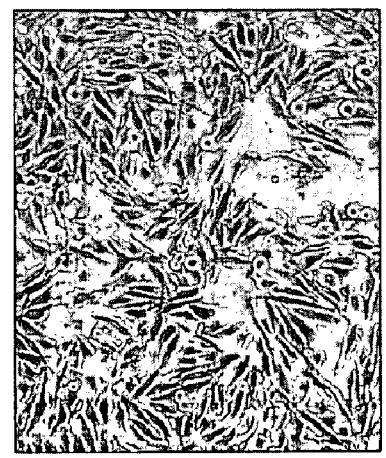
Figure 11:
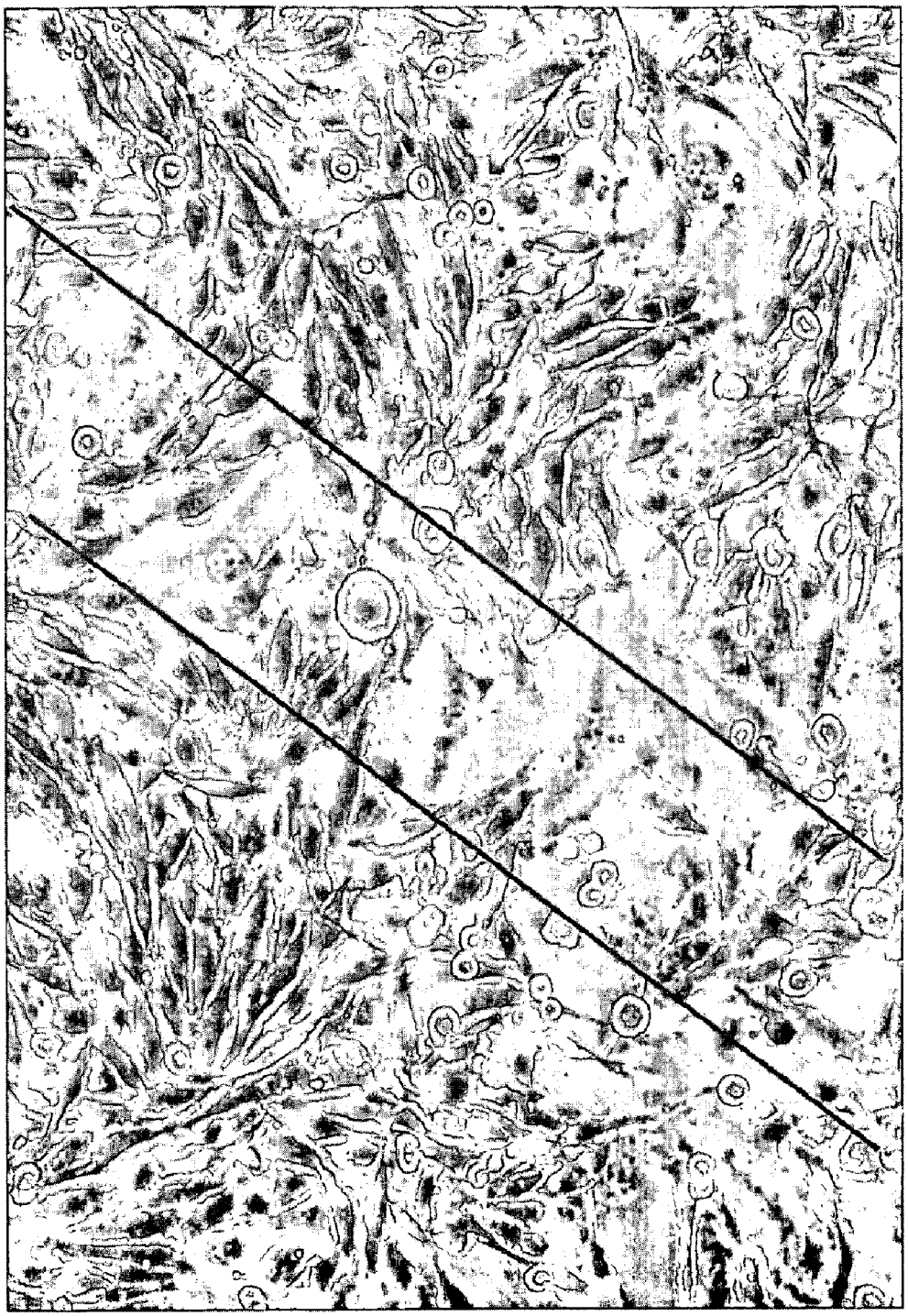
FIG. 11 shows the measuring of the width of a parting under a phase contrast microscope for the cell migration assay.
Figure 12:
FIG. 12 is an exemplary measuring of the cell migration assay in the presence of letrozole.
Figure 12:
Figure 12:
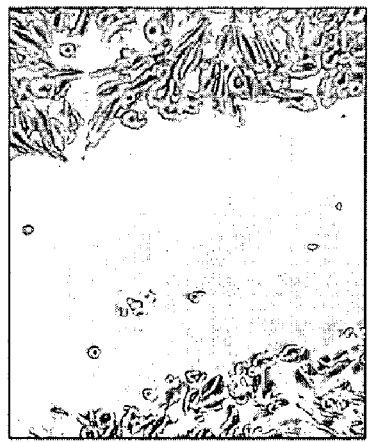
Figure 12:
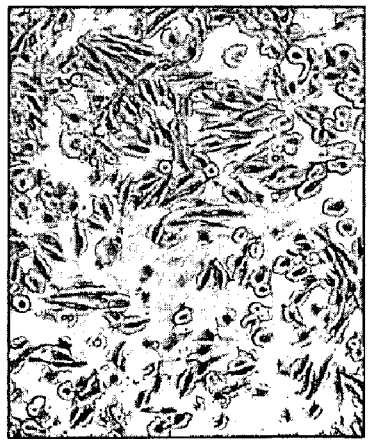
Figure 13:
FIG. 13 is an exemplary measuring of the cell migration assay in the presence of entinostat (MS-275).
Figure 13:
Figure 13:
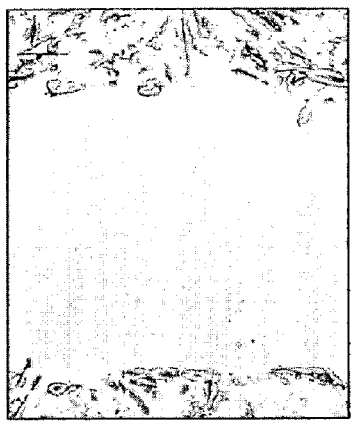
Figure 13:
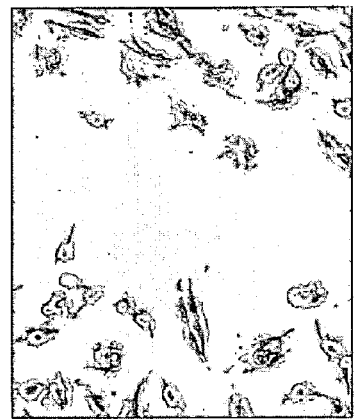
Figure 13:
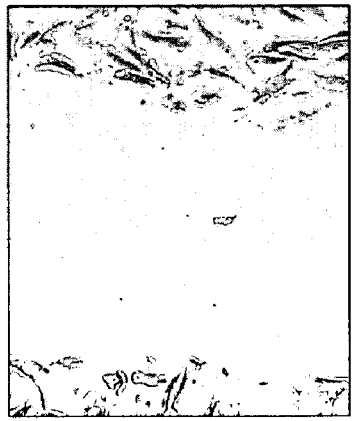
Figure 13:
Figure 14:
FIG. 14 demonstrates the cell migration assay in the presence of the combination of entinostat and letrozole.
Figure 14:
Figure 15:
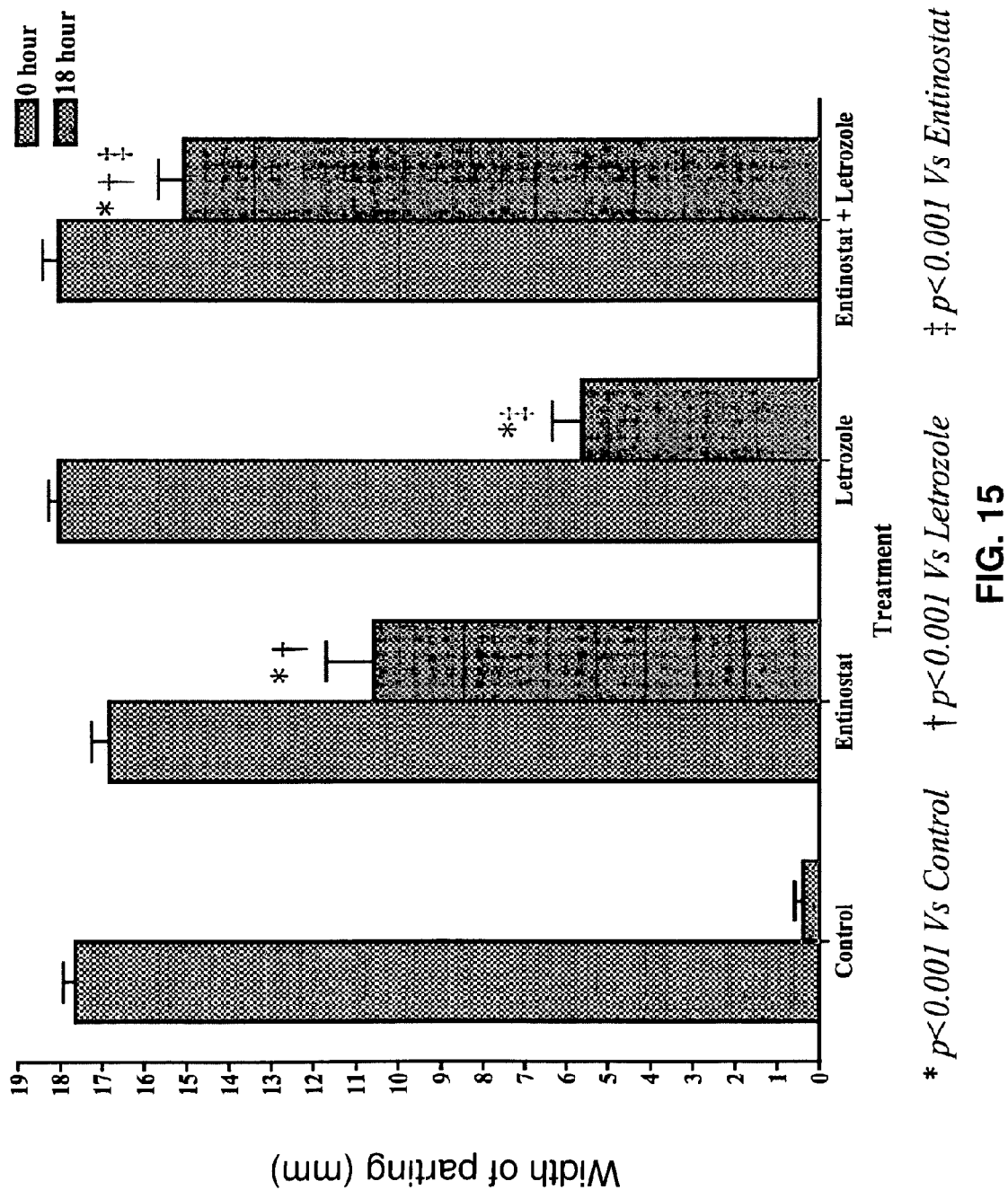
FIG. 15 graphically illustrates the width of parting in the cell migration assay and compares the width at 0 hours and 18 hours for the various cell treatments.

MDA-MB-231 cells were plated into 60 mm² cell culture dishes and allowed to grow till 80% confluent. The medium was removed and cells were washed with DPBS twice. The cell monolayer was scraped to make an open parting and the cells were washed twice with DPBS. The cells were then treated with indicated agents for 18 hours. The parting was photographed under phase contrast microscope at 0 hour and 18 hour time point. The width of the open parting was measured by the on-screen ruler on the microscope camera. Each parting was measured at 4 locations and the mean distance recorded (see FIG. 11 for an example). The distance traveled by the migrating cells across the parting at the end of 18 hours was compared to the initial distance and reported as "width of the open parting". The migratory behavior of the cells in this assay may be correlated with the invasive properties of tumor cells and/or tumor progression. FIG. 10 gives an example of the migration of control cells without treatment. FIG. 12 and FIG. 13 gives an example of the migration of cells in the presence of letrozole or entinostat (MS-275), respectively, and FIG. 14 demonstrates the cell migration assay in the presence of the combination of entinostat and letrozole. The results of the cell migration assay are summarized in FIGS. 15-16, showing that the combination therapy is more effective than either agent alone at limiting cell migration. The combination effectively prevented cell migration, and in specific embodiments combinations of HDACi and hormone targeted drugs are useful for preventing metastasis of cancer cells.

Example 10

Molecular Effects of HDACI Androgen Negative Prostate Cancer Cells

Methods:
Cell Viability Assessment Using MTT Assay:
MTT assay is performed to measure viability of prostate cancer cells after treatment with various test compounds (Sabnis et al. 2005). $IC_{50}$ and $IC_{25}$ values for inhibitors is calculated from the linear regression line of the plot of percentage inhibition versus log inhibitor concentration. These $IC_{50}$ values is used for combination or sequencing studies. The effect of combination or sequence of treatment is be determined at $IC_{25}$ of each agent.
Western Immunoblotting for Expression of Androgen Receptor and Downstream Targets:
The protein extracts from prostate cancer cells are subjected to western immunoblotting (Sabnis et al., 2005). Protein expression of androgen receptor are examined following HDACi treatment.

Androgen Activity Measurement:
To measure the transcriptional activity of re-expressed androgen receptor in the androgen receptor negative-cells ELISA based activity assay are used. This assay is performed on nuclear extracts of untreated or HDACi pretreated malignant prostate cells preparation of nuclear extracts and activity assay is performed as per manufacture's instructions (Panomics).
Cell Proliferation in Response to Androgens:
To examine whether pre-treatment with HDACi, restores mitogenic effects of androgens, non-malignant and malignant prostate cells are pre-treated with HDACi followed by treatment with an androgen and the viability of cells measured by MTT assay.

Example 11

Human Clinical Trial of the Safety and Efficacy of Combination of HDAC Inhibitor and Aromatase Inhibitor Objective: To compare the safety and pharmacokinetics of administered HDAC inhibitor and Aromatase Inhibitor.
Study Design: This will be a Phase I, single-center, open-label, randomized dose escalation study followed by a Phase II study in breast cancer patients with disease that can be biopsied. Patients should not have had exposure to the HDAC inhibitor or Aromatase Inhibitor prior to the study entry. Patients must not have received treatment for their cancer within 2 weeks of beginning the trial. Treatments include the use of chemotherapy, hematopoietic growth factors, and biologic therapy such as monoclonal antibodies. All subjects are evaluated for safety and all blood collections for pharmacokinetic analysis are collected as scheduled. All studies are performed with institutional ethics committee approval and patient consent.
Phase I: Patients receive an aromatase inhibitor and HDAC inhibitor according to a pre-determined dosing regimen. Cohorts of 3-6 patients receive escalating doses of the aromatase inhibitor and the HDAC inhibitor until the maximum tolerated dose (MTD) for the combination is determined. Test dose ranges are initially determined via the established individual dose ranges for the aromatase inhibitor and the HDAC inhibitor. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CT-CAE) Version 3.0 (Aug. 9, 2006).
Phase II: Patients receive the aromatase inhibitor as in phase I at the MTD determined in phase I and the HDAC inhibitor as in phase I. Treatment repeats every 6 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.
Blood Sampling: Serial blood is drawn by direct vein puncture before and after administration of the HDAC inhibitor and/or the HMT inhibitor. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration (Cmax); time to peak serum concentration (tmax); area under the concentration-time curve (AUC) from time zero to the last blood sampling time (AUC0-72) calculated with the use of the linear trapezoidal rule; and terminal elimination half-life (t½), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 12

Administration of MS-275 and Letrazole for Treatment of Breast Cancer

According to Example 11, a Human Clinical Trial of the Safety and/or Efficacy of MS-275/letrazole combination therapy is performed. The breast cancer patients have not had exposure to either MS-275 or letrazole prior to the study entry and have not received treatment for their cancer within 2 weeks of beginning the trial. In conclusion, administration of a combination of MS-275 and letrazole will be safe and well tolerated by cancer patients. The combination of MS-275 and letrazole provides large clinical utility to these cancer patients.

Example 13

Administration of MS-275 and Anastrazole for Treatment of Breast Cancer

According to Example 11, a Human Clinical Trial of the Safety and/or Efficacy of MS-275/anastrazole combination therapy is performed. The breast cancer patients have not had exposure to either MS-275 or anastrazole prior to the study entry and have not received treatment for their cancer within 2 weeks of beginning the trial. In conclusion, administration of a combination of MS-275 and anastrazole will be safe and well tolerated by cancer patients. The combination of MS-275 and anastrazole provides large clinical utility to these cancer patients.

Example 14

Administration of MS-275 and Exemestane for Treatment of Breast Cancer

According to Example 11, a Human Clinical Trial of the Safety and/or Efficacy of MS-275/exenestane combination therapy is performed. The breast cancer patients have not had exposure to either MS-275 or exemestane prior to the study entry and have not received treatment for their cancer within 2 weeks of beginning the trial. In conclusion, administration of a combination of MS-275 and exemestane will be safe and well tolerated by cancer patients. The combination of MS-275 and exemestane provides large clinical utility to these cancer patients.

Example 15

Administration of SAHA and Letrazole for Treatment of Breast Cancer

According to Example 11, a Human Clinical Trial of the Safety and/or Efficacy of SAHA/letrazole combination therapy is performed. The breast cancer patients have not had exposure to either SAHA or letrazole prior to the study entry and have not received treatment for their cancer within 2 weeks of beginning the trial. In conclusion, administration of a combination of SAHA and letrazole will be safe and well tolerated by cancer patients. The combination of SAHA and letrazole provides large clinical utility to these cancer patients.

Example 16

Administration of SAHA and Anastrazole for Treatment of Breast Cancer

According to Example 11, a Human Clinical Trial of the Safety and/or Efficacy of SAHA/anastrazole combination therapy is performed. The breast cancer patients have not had exposure to either SAHA or anastrazole prior to the study entry and have not received treatment for their cancer within 2 weeks of beginning the trial. In conclusion, administration of a combination of SAHA and anastrazole will be safe and well tolerated by cancer patients. The combination of SAHA and anastrazole provides large clinical utility to these cancer patients.

Example 17

Administration of SAHA and Exemestane for Treatment of Breast Cancer

According to Example 11, a Human Clinical Trial of the Safety and/or Efficacy of SAHA/exenestane combination therapy is performed. The breast cancer patients have not had exposure to either SAHA or exemestane prior to the study entry and have not received treatment for their cancer within 2 weeks of beginning the trial. In conclusion, administration of a combination of SAHA and exemestane will be safe and well tolerated by cancer patients. The combination of SAHA and exemestane provides large clinical utility to these cancer patients.

Example 18

Administration of MGCD-0103 and Letrazole for Treatment of Breast Cancer

According to Example 11, a Human Clinical Trial of the Safety and/or Efficacy of MS MGCD-0103/letrazole combination therapy is performed. The breast cancer patients have not had exposure to either MGCD-0103 or letrazole prior to the study entry and have not received treatment for their cancer within 2 weeks of beginning the trial. In conclusion, administration of a combination of MGCD-0103 and letrazole will be safe and well tolerated by cancer patients. The combination of MGCD-0103 and letrazole provides large clinical utility to these cancer patients.

Example 19

Administration of MGCD-0103 and Anastrazole for Treatment of Breast Cancer

According to Example 11, a Human Clinical Trial of the Safety and/or Efficacy of MGCD-0103/anastrazole combination therapy is performed. The breast cancer patients have not had exposure to either MGCD-0103 or anastrazole prior to the study entry and have not received treatment for their cancer within 2 weeks of beginning the trial. In conclusion, administration of a combination of MGCD-0103 and anastrazole will be safe and well tolerated by cancer patients. The combination of MGCD-0103 and anastrazole provides large clinical utility to these cancer patients.

Example 20

Administration of MGCD-0103 and Exemestane for Treatment of Breast Cancer

According to Example 11, a Human Clinical Trial of the Safety and/or Efficacy of MGCD-0103/exenestane combination therapy is performed. The breast cancer patients have not had exposure to either MGCD-0103 or exemestane prior to the study entry and have not received treatment for their cancer within 2 weeks of beginning the trial. In conclusion, administration of a combination of MGCD-0103 and exemestane will be safe and well tolerated by cancer patients. The combination of MGCD-0103 and exemestane provides large clinical utility to these cancer patients.

Example 21

Administration of FK228 and Letrazole for Treatment of Breast Cancer

According to Example 11, a Human Clinical Trial of the Safety and/or Efficacy of FK228/letrazole combination therapy is performed. The breast cancer patients have not had exposure to either FK228 or letrazole prior to the study entry and have not received treatment for their cancer within 2 weeks of beginning the trial. In conclusion, administration of a combination of FK228 and letrazole will be safe and well tolerated by cancer patients. The combination of FK228 and letrazole provides large clinical utility to these cancer patients.

Example 22

Administration of FK228 and Anastrazole for Treatment of Breast Cancer

According to Example 11, a Human Clinical Trial of the Safety and/or Efficacy of FK228/anastrazole combination therapy is performed. The breast cancer patients have not had exposure to either FK228 or anastrazole prior to the study entry and have not received treatment for their cancer within 2 weeks of beginning the trial. In conclusion, administration of a combination of FK228 and anastrazole will be safe and well tolerated by cancer patients. The combination of FK228 and anastrazole provides large clinical utility to these cancer patients.

Example 23

Administration of FK-228 and Exemestane for Treatment of Breast Cancer

According to Example 11, a Human Clinical Trial of the Safety and/or Efficacy of FK228/exenestane combination therapy is performed. The breast cancer patients have not had exposure to either FK228 or exemestane prior to the study entry and have not received treatment for their cancer within 2 weeks of beginning the trial. In conclusion, administration of a combination of FK228 and exemestane will be safe and well tolerated by cancer patients. The combination of FK228 and exemestane provides large clinical utility to these cancer patients.

Example 24

Administration of LBH589 and Letrazole for Treatment of Breast Cancer

According to Example 11, a Human Clinical Trial of the Safety and/or Efficacy of LBH589/letrazole combination therapy is performed. The breast cancer patients have not had exposure to either LBH589 or letrazole prior to the study entry and have not received treatment for their cancer within 2 weeks of beginning the trial. In conclusion, administration of a combination of LBH589 and letrazole will be safe and well tolerated by cancer patients. The combination of LBH589 and letrazole provides large clinical utility to these cancer patients.

Example 25

Administration of LBH589 and Anastrazole for Treatment of Breast Cancer

According to Example 11, a Human Clinical Trial of the Safety and/or Efficacy of LBH589/anastrazole combination therapy is performed. The breast cancer patients have not had exposure to either LBH589 or anastrazole prior to the study entry and have not received treatment for their cancer within 2 weeks of beginning the trial. In conclusion, administration of a combination of LBH589 and anastrazole will be safe and well tolerated by cancer patients. The combination of LBH589 and anastrazole provides large clinical utility to these cancer patients.

Example 26

Administration of LBH589 and Exemestane for Treatment of Breast Cancer

According to Example 11, a Human Clinical Trial of the Safety and/or Efficacy of LBH589/exenestane combination therapy is performed. The breast cancer patients have not had exposure to either LBH589 or exemestane prior to the study entry and have not received treatment for their cancer within 2 weeks of beginning the trial. In conclusion, administration of a combination of LBH589 and exemestane will be safe and well tolerated by cancer patients. The combination of LBH589 and exemestane provides large clinical utility to these cancer patients.

Example 27

Human Clinical Trial of the Safety and Efficacy of Combination of HDAC Inhibitor and Anti-Androgen Objective: To compare the safety and pharmacokinetics of administered HDAC inhibitor and Anti-Androgen.

Study Design: This will be a Phase I, single-center, open-label, randomized dose escalation study followed by a Phase II study in prostate cancer patients with disease that can be biopsied. Patients should not have had exposure to the HDAC inhibitor or Anti-Androgen prior to the study entry. Patients must not have received treatment for their cancer within 2 weeks of beginning the trial. Treatments include the use of chemotherapy, hematopoietic growth factors, and biologic therapy such as monoclonal antibodies. All subjects are evaluated for safety and all blood collections for pharmacokinetic analysis are collected as scheduled. All studies are performed with institutional ethics committee approval and patient consent.

Phase I: Patients receive an aromatase inhibitor and HDAC inhibitor according to a pre-determined dosing regimen. Cohorts of 3-6 patients receive escalating doses of the anti-androgen and the HDAC inhibitor until the maximum tolerated dose (MTD) for the combination is determined. Test dose ranges are initially determined via the established individual dose ranges for the anti-androgen and the HDAC inhibitor. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CT-CAE) Version 3.0 (Aug. 9, 2006).

Phase II: Patients receive the anti-androgen as in phase I at the MTD determined in phase I and the HDAC inhibitor as in phase I. Treatment repeats every 6 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling: Serial blood is drawn by direct vein puncture before and after administration of the HDAC inhibitor and/or the HMT inhibitor. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration (Cmax); time to peak serum concentration (tmax); area under the concentration-time curve (AUC) from time zero to the last blood sampling time (AUC0-72) calculated with the use of the linear trapezoidal rule; and terminal elimination half-life (t½), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al., J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 28

Administration of LBH589 and Spironolactone for Treatment of Prostate Cancer

According to Example 27, a Human Clinical Trial of the Safety and/or Efficacy of LBH589/spironolactone combination therapy is performed. The prostate cancer patients have not had exposure to either LBH589 or spironolactone prior to the study entry and have not received treatment for their cancer within 2 weeks of beginning the trial. In conclusion, administration of a combination of LBH589 and spironolactone will be safe and well tolerated by cancer patients. The combination of LBH589 and spironolactone provides large clinical utility to these cancer patients.

Example 29

Administration of LBH589 and Flutamide for Treatment of Prostate Cancer

According to Example 27, a Human Clinical Trial of the Safety and/or Efficacy of LBH589/flutamide combination therapy is performed. The prostate cancer patients have not had exposure to either LBH589 or flutamide prior to the study entry and have not received treatment for their cancer within 2 weeks of beginning the trial. In conclusion, administration of a combination of LBH589 and flutamide will be safe and well tolerated by cancer patients. The combination of LBH589 and flutamide provides large clinical utility to these cancer patients.

Example 30

Administration of LBH589 and Nilutamide for Treatment of Prostate Cancer

According to Example 27, a Human Clinical Trial of the Safety and/or Efficacy of LBH589/nilutamide combination therapy is performed. The prostate cancer patients have not had exposure to either LBH589 or nilutamide prior to the study entry and have not received treatment for their cancer within 2 weeks of beginning the trial. In conclusion, administration of a combination of LBH589 and nilutamide will be safe and well tolerated by cancer patients. The combination of LBH589 and nilutamide provides large clinical utility to these cancer patients.

Example 31

Administration of LBH589 and Bicalutamide for Treatment of Prostate Cancer

According to Example 27, a Human Clinical Trial of the Safety and/or Efficacy of LBH589/bicalutamide combination therapy is performed. The prostate cancer patients have not had exposure to either LBH589 or bicalutamide prior to the study entry and have not received treatment for their cancer within 2 weeks of beginning the trial. In conclusion, administration of a combination of LBH589 and bicalutamide will be safe and well tolerated by cancer patients. The combination of LBH589 and bicalutamide provides large clinical utility to these cancer patients.

Example 32

Administration of SAHA and Spironolactone for Treatment of Prostate Cancer

According to Example 27, a Human Clinical Trial of the Safety and/or Efficacy of SAHA/spironolactone combination therapy is performed. The prostate cancer patients have not had exposure to either SAHA or spironolactone prior to the study entry and have not received treatment for their cancer within 2 weeks of beginning the trial. In conclusion, administration of a combination of SAHA and spironolactone will be safe and well tolerated by cancer patients. The combination of SAHA and spironolactone provides large clinical utility to these cancer patients.

Example 33

Administration of SAHA and Flutamide for Treatment of Prostate Cancer

According to Example 27, a Human Clinical Trial of the Safety and/or Efficacy of SAHA/flutamide combination therapy is performed. The prostate cancer patients have not had exposure to either SAHA or flutamide prior to the study entry and have not received treatment for their cancer within 2 weeks of beginning the trial. In conclusion, administration of a combination of SAHA and flutamide will be safe and well tolerated by cancer patients. The combination of SAHA and flutamide provides large clinical utility to these cancer patients.

Example 34

Administration of SAHA and Nilutamide for Treatment of Prostate Cancer

According to Example 27, a Human Clinical Trial of the Safety and/or Efficacy of SAHA/nilutamide combination therapy is performed. The prostate cancer patients have not had exposure to either SAHA or nilutamide prior to the study entry and have not received treatment for their cancer within 2 weeks of beginning the trial. In conclusion, administration of a combination of SAHA and nilutamide will be safe and well tolerated by cancer patients. The combination of SAHA and nilutamide provides large clinical utility to these cancer patients.

Example 35

Administration of SAHA and Bicalutamide for Treatment of Prostate Cancer

According to Example 27, a Human Clinical Trial of the Safety and/or Efficacy of SAHA/bicalutamide combination therapy is performed. The prostate cancer patients have not had exposure to either SAHA or bicalutamide prior to the study entry and have not received treatment for their cancer within 2 weeks of beginning the trial. In conclusion, administration of a combination of SAHA and bicalutamide will be safe and well tolerated by cancer patients. The combination of SAHA and bicalutamide provides large clinical utility to these cancer patients.

Example 36

Administration of MGCD-0103 and Spironolactone for Treatment of Prostate Cancer

According to Example 27, a Human Clinical Trial of the Safety and/or Efficacy of MGCD-0103/spironolactone combination therapy is performed. The prostate cancer patients have not had exposure to either MGCD-0103 or spironolactone prior to the study entry and have not received treatment for their cancer within 2 weeks of beginning the trial. In conclusion, administration of a combination of MGCD-0103 and spironolactone will be safe and well tolerated by cancer patients. The combination of MGCD-0103 and spironolactone provides large clinical utility to these cancer patients.

Example 37

Administration of MGCD-0103 and Flutamide for Treatment of Prostate Cancer

According to Example 27, a Human Clinical Trial of the Safety and/or Efficacy of MGCD-0103/flutamide combination therapy is performed. The prostate cancer patients have not had exposure to either MGCD-0103 or flutamide prior to the study entry and have not received treatment for their cancer within 2 weeks of beginning the trial. In conclusion, administration of a combination of MGCD-0103 and flutamide will be safe and well tolerated by cancer patients. The combination of MGCD-0103 and flutamide provides large clinical utility to these cancer patients.

Example 38

Administration of MGCD-0103 and Nilutamide for Treatment of Prostate Cancer

According to Example 27, a Human Clinical Trial of the Safety and/or Efficacy of MGCD-0103/nilutamide combination therapy is performed. The prostate cancer patients have not had exposure to either MGCD-0103 or nilutamide prior to the study entry and have not received treatment for their cancer within 2 weeks of beginning the trial. In conclusion, administration of a combination of MGCD-0103 and nilutamide will be safe and well tolerated by cancer patients. The combination of MGCD-0103 and nilutamide provides large clinical utility to these cancer patients.

Example 39

Administration of MGCD-0103 and Bicalutamide for Treatment of Prostate Cancer

According to Example 27, a Human Clinical Trial of the Safety and/or Efficacy of MGCD-0103/bicalutamide combination therapy is performed. The prostate cancer patients have not had exposure to either MGCD-0103 or bicalutamide prior to the study entry and have not received treatment for their cancer within 2 weeks of beginning the trial. In conclusion, administration of a combination of MGCD-0103 and bicalutamide will be safe and well tolerated by cancer patients. The combination of MGCD-0103 and bicalutamide provides large clinical utility to these cancer patients.

Example 40

Administration of MS-275 and Spironolactone for Treatment of Prostate Cancer

According to Example 27, a Human Clinical Trial of the Safety and/or Efficacy of MS-275/spironolactone combination therapy is performed. The prostate cancer patients have not had exposure to either MS-275 or spironolactone prior to the study entry and have not received treatment for their cancer within 2 weeks of beginning the trial. In conclusion, administration of a combination of MS-275 and spironolactone will be safe and well tolerated by cancer patients. The combination of MS-275 and spironolactone provides large clinical utility to these cancer patients.

Example 41

Administration of MS-275 and Flutamide for Treatment of Prostate Cancer

According to Example 27, a Human Clinical Trial of the Safety and/or Efficacy of MS-275/flutamide combination therapy is performed. The prostate cancer patients have not had exposure to either MS-275 or flutamide prior to the study entry and have not received treatment for their cancer within 2 weeks of beginning the trial. In conclusion, administration of a combination of MS-275 and flutamide will be safe and well tolerated by cancer patients. The combination of MS-275 and flutamide provides large clinical utility to these cancer patients.

Example 42

Administration of MS-275 and Nilutamide for Treatment of Prostate Cancer

According to Example 27, a Human Clinical Trial of the Safety and/or Efficacy of MS-275/nilutamide combination therapy is performed. The prostate cancer patients have not had exposure to either MS-275 or nilutamide prior to the study entry and have not received treatment for their cancer within 2 weeks of beginning the trial. In conclusion, administration of a combination of MS-275 and nilutamide will be safe and well tolerated by cancer patients. The combination of MS-275 and nilutamide provides large clinical utility to these cancer patients.

Example 43

Administration of MS-275 and Bicalutamide for Treatment of Prostate Cancer

According to Example 27, a Human Clinical Trial of the Safety and/or Efficacy of MS-275/bicalutamide combination therapy is performed. The prostate cancer patients have not had exposure to either MS-275 or bicalutamide prior to the study entry and have not received treatment for their cancer within 2 weeks of beginning the trial. In conclusion, administration of a combination of MS-275 and bicalutamide will be safe and well tolerated by cancer patients. The combination of MS-275 and bicalutamide provides large clinical utility to these cancer patients.

Example 44

Administration of FK228 and Spironolactone for Treatment of Prostate Cancer

According to Example 27, a Human Clinical Trial of the Safety and/or Efficacy of FK228/spironolactone combination therapy is performed. The prostate cancer patients have not had exposure to either FK228 or spironolactone prior to the study entry and have not received treatment for their cancer within 2 weeks of beginning the trial. In conclusion, administration of a combination of FK228 and spironolactone will be safe and well tolerated by cancer patients. The combination of FK228 and spironolactone provides large clinical utility to these cancer patients.

Example 45

Administration of FK228 and Flutamide for Treatment of Prostate Cancer

According to Example 27, a Human Clinical Trial of the Safety and/or Efficacy of FK228/flutamide combination therapy is performed. The prostate cancer patients have not had exposure to either FK228 or flutamide prior to the study entry and have not received treatment for their cancer within 2 weeks of beginning the trial. In conclusion, administration of a combination of FK228 and flutamide will be safe and well tolerated by cancer patients. The combination of FK228 and flutamide provides large clinical utility to these cancer patients.

Example 46

Administration of FK228 and Nilutamide for Treatment of Prostate Cancer

According to Example 27, a Human Clinical Trial of the Safety and/or Efficacy of FK228/nilutamide combination therapy is performed. The prostate cancer patients have not had exposure to either FK228 or nilutamide prior to the study entry and have not received treatment for their cancer within 2 weeks of beginning the trial. In conclusion, administration of a combination of FK228 and nilutamide will be safe and well tolerated by cancer patients. The combination of FK228 and nilutamide provides large clinical utility to these cancer patients.

Example 47

Administration of FK228 and Bicalutamide for Treatment of Prostate Cancer

According to Example 27, a Human Clinical Trial of the Safety and/or Efficacy of FK228/bicalutamide combination therapy is performed. The prostate cancer patients have not had exposure to either FK228 or bicalutamide prior to the study entry and have not received treatment for their cancer within 2 weeks of beginning the trial. In conclusion, administration of a combination of FK228 and bicalutamide will be safe and well tolerated by cancer patients. The combination of FK228 and bicalutamide provides large clinical utility to these cancer patients.

REFERENCES

The following references, to the extent that they provide exemplary procedural or other details supplementary to those set forth herein, are specifically incorporated herein by reference.

Alexander, J. et al., J Med Chem 1988, 31, (2), 318-22.
Baum, M et al., Lancet 2002, 359, (9324), 2131-9.
Baum, M., Eur J Cancer 2002, 38, (15), 1984-6.
Belosay, A. et al., The Endocrine Society's 88th Annual Meeting, Boston, Mass., 2005; Boston, Mass., 2005.
Boasberg, et al., Proc. Am. Soc. Clin. Oncol. 16:1126, 1997.
Brodie, A. M. et al., Endocrinology 1977, 100, (6), 1684-95.
Brodie, A., J Enzyme Inhib 1990, 4, (2), 75-7.
Cheng, et al., In: Prostate Diseases, edited by H. Lepor and R. K. Lawson. 1993, p. 57-71.
Chiarodo, Cancer Res. 51:2498-2505, 1991.
Conley, B. A.; et al., Cancer 2006, 107, (4), 832-40.
Folkman, N. Engl. J. Med. 285:1182-1186, 1971.
Folkman, Nat. Med. 1:27-31, 1995.
Fulton, A. M. et al., Cancer Res 2006, 66, (20), 9794-7.
Fuqua, et al., Endocr. Relat. Cancer 2:19-25, 1995.
Gao, et al., Prostate 31:264-281, 1997.
Gediya, L. K. et al., J Med Chem 2005, 48, (15), 5047-51.
Goss, P. E et al., Drugs 2002, 62, (6), 957-66.
Goss, P. E et al., J Natl Cancer Inst 2005, 97, (17), 1262-71.
Greenwald, R. B. et al., J Med Chem 1999, 42, (18), 3657-67.
Hopp and Fuqua, J. Mammary Gland Biol. and Neoplasia 3:73-83, 1999.
Jelovac, D. et al., Cancer Res 2005, 65, (12), 5439-44.
Jemal, A, et al., CA Cancer J Clin 2006, 56, (2), 106-30.
Jordan, V. C et al., Steroids 2007, 72, (1), 7-25.
Keen, J. C et al., Breast Cancer Res Treat 2003, 81, (3), 177-86.
Kelly, et al., Proc. Am. Soc. Clin. Oncol. 15:250, 1996.
Kelly, W. K. et al., J Clin Oncol 2005, 23, (17), 3923-31.
Klotz, Cancer 88:3009-3014, 2000.
Klotz, Cancer 88:3009-3014, 2000.
Knox, et al., Prostate 35:248-254, 1998.
Knox, et al., Prostate 35:248-254, 1998.
Kubota, et al., Cancer Res. 58:3344-3352, 1998.
Landis, et al., Cancer J. Clin. 48:6-29, 1998.
Long, B. J. et al., Clin Cancer Res 2002, 8, (7), 2378-88.
Long, B. J. et al., J Natl Cancer Inst 2004, 96, (6), 456-65.
Lu Q et al., Breast Cancer Res Treat, 57:183-192, 1999.
Margueron, R et al., Biochem Pharmacol 2004, 68, (6), 1239-46.
Miller, et al., Cancer Res. 52:515-520, 1992.
Miller, et al., Clin. Cancer Res. 1:997-1003, 1995.
Morris and Scher, Cancer 89:1329-1348, 2000.
Nudelman, A. et al., J Med Chem 2000, 43, (15), 2962-6.
Peehl, et al., Cancer Res. 54:805-810, 1994.
Pienta, et al., Cancer Res. 53:224-226, 1993.
Pollard, et al., Cancer Res. 51:3610-3611, 1991.
Ravdin, P et al., In San Antonio Breast Cancer Symposium, San Antonio, Tex., Breast Cancer Research and Treatment: 2006
Ryan, Q. C. et al., J Clin Oncol 2005, 23, (17), 3912-22.
Sabnis, G. J. et al., Cancer Res 2005, 65, (9), 3903-10.
Sadar, et al., Endocr. Relat. Cancer 6:487-502, 1999.
Sakti and Crawford. Cancer of the Prostate. New York: Marcel Dekker, 1993. p. 1.
Sharma, D et al., Cancer Res 2006, 66, (12), 6370-8.
Shibata, et al., J. Natl. Cancer Inst. 90:1230-1231, 1998.
Smith, et al., Proc. Am. Soc. Clin. Oncol. 18:328, 1999.
Suzuki, T. et al., J Med Chem 1999, 42, (15), 3001-3.
Takabatake, D. et al., Int J Cancer 2007, 120, (1), 181-8.
Tontonoz, et al., Cell 79:1147-1156, 1994.
Tontonoz, et al., Proc. Natl. Acad. Sci. U.S.A. 94:237-241, 1997.
Vigushin, D. M. et al., Anticancer Drugs 2002, 13, (1), 1-13.
Walser, T. C. et al., Cancer Res 2006, 66, (15), 7701-7.
Yamaoka, et al., Cancer Res. 53:5233-5236, 1993.
Yang, X et al., Cancer Res 2000, 60, (24), 6890-4.
Yu, D. D et al., J Org Chem 2003, 68, (24), 9489-91.
Yue W, and Brodie A J Steroid Biochem Mol Biol, 63:317-328, 1997.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating an estrogen receptor negative breast cancer in a subject having the estrogen resistant breast cancer, comprising the step of administering to the subject an effective amount of the following:
   histone deacetylase inhibitor MS-275; and
   an aromatase inhibitor selected from the group consisting of anastrozole, exemestane, and letrozole.

2. The method of claim 1, wherein the breast cancer is ER−, PR+.

3. The method of claim 1, wherein the breast cancer is ER−, PR− and Her2+.

4. The method of claim 1, wherein the breast cancer is ER−, PR− and Her2−.

5. A method of inhibiting growth of an estrogen receptor negative breast cancer cell comprising contacting the cell with an aromatase inhibitor and MS-275, each in an effective amount to inhibit growth of said cell, wherein the aromatase inhibitor is selected from the group consisting of anastrozole, exemestane, and letrozole.

6. The method of claim 5, wherein the estrogen receptor negative breast cancer cell is resistant to estrogen by acquired resistance.

7. The methods method of claim 5, wherein deacetylase inhibitor MS-275 increases the expression of an estrogen receptor on the cell.

8. The method of claim 5, wherein MS-275 increases the expression or activity of aromatase in the cell.

9. The method of claim 5, wherein the contacting occurs in vivo.

10. The method of claim 6, wherein the hormone resistance is acquired resistance.

11. A method of treating estrogen receptor negative breast cancer in an individual, comprising the steps of:
administering MS-275 to the individual in an amount effective to upregulate expression of the estrogen receptor in estrogen receptor negative breast cancer cells; and
administering to the individual an aromatase inhibitor in an amount effective to treat the cancer, wherein the aromatase inhibitor is selected from the group consisting of anastrozole, exemestane, and letrozole.

12. The method of claim 11, wherein the estrogen receptor negative breast cancer is PR negative and HER2 negative.

13. The method of claim 1, wherein MS-275 and the aromatase inhibitor are administered simultaneously.

14. The method of claim 1, wherein MS-275 is administered prior to the administration of the aromatase inhibitor.

15. The method of claim 1, wherein MS-275 is administered subsequent to the administration of one or more dose of the aromatase inhibitor.

16. The method of claim 1, wherein MS-275 and the aromatase inhibitor act synergistically.

* * * * *

UNITED STATES PATENT AND TRADEMARK OFFICE
CERTIFICATE OF CORRECTION

PATENT NO. : 8,110,550 B2  
APPLICATION NO. : 12/134717  
DATED : February 7, 2012  
INVENTOR(S) : Angela Brodie et al.

Page 1 of 1

It is certified that error appears in the above-identified patent and that said Letters Patent is hereby corrected as shown below:

Column 2, line 14, please amend as follows:

\*\* This invention was made "in part" with government support under Grant "Nos." --Numbers-- RO1 CA-62483 and R21 CA117991 awarded by the National Institutes of Health. The "United States Government" --government-- has certain rights in the invention.\*\*

Signed and Sealed this
Nineteenth Day of June, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO. : 8,110,550 B2
APPLICATION NO. : 12/134717
DATED : February 7, 2012
INVENTOR(S) : Angela Brodie et al.

It is certified that error appears in the above-identified patent and that said Letters Patent is hereby corrected as shown below:

Column 1, line 14, please amend as follows:

\*\* This invention was made with government support under Grant Numbers CA062483 and CA117991 awarded by the National Institutes of Health. The government has certain rights in the invention.\*\*

This certificate supersedes the Certificate of Correction issued June 19, 2012.

Signed and Sealed this
First Day of January, 2013

David J. Kappos
*Director of the United States Patent and Trademark Office*